US006943253B2

(12) United States Patent
Vidal Juan et al.

(10) Patent No.: US 6,943,253 B2
(45) Date of Patent: Sep. 13, 2005

(54) 6-PHENYLPYRROLOPYRIMIDINEDIONE DERIVATIVES

(75) Inventors: Bernat Vidal Juan, Sant Cebria de Vallalta (ES); Jordi Gracia Ferrer, Barcelona (ES); José Manuel Prieto Soto, Barcelona (ES); Armando Vega Noverola, Barcelona (ES)

(73) Assignee: Almirall Prodesfarma S.A., Barcelona (ES)

( * ) Notice: Subject to any disclaimer, the term of this patent is extended or adjusted under 35 U.S.C. 154(b) by 66 days.

(21) Appl. No.: 10/313,922

(22) Filed: Dec. 6, 2002

(65) Prior Publication Data

US 2003/0232838 A1 Dec. 18, 2003

Related U.S. Application Data

(63) Continuation of application No. PCT/EP01/06306, filed on Jun. 1, 2001.

(30) Foreign Application Priority Data

Jun. 7, 2000 (ES) .......................................... 200001436

(51) Int. Cl.$^7$ .................... C07D 487/04; A61K 31/519
(52) U.S. Cl. .................... 544/357; 544/383; 564/88; 514/234.2; 514/252.16; 514/265.1
(58) Field of Search .................... 514/234.2, 252.16, 514/265.1; 544/158, 280, 357, 383; 564/88

(56) References Cited

U.S. PATENT DOCUMENTS 6,214,882 B1 * 4/2001 Purcell et al. .............. 514/602

FOREIGN PATENT DOCUMENTS

EP          0 480 659 A2    4/1992
WO         WO 99/62905    12/1999

OTHER PUBLICATIONS

Perry, M.J. et al, Current Opinion in Chemical Biology, 1998, 2, 472–481.*
Corbin JD, Francis SH., Int J Clin Pract. Jul.–Aug. 2002;56(6):453–9.*
Cremers B, Bohm M., Herz. Jun. 2003;28(4):325–33.*
Covello, M. and Piscopo, E. (1964). "Nuovi Iodo–Organici di Sintesi. Preparazione di O–Alchilossibenzaldeidi, O–Alchilossiacetofenoni Ed. Analoghi IOdurati," *Nuovi Iodo–Organici di Sintesi, Il Farmaco, Ed. Sc.* vol. 19, Fascicule 8, 675–687 with English Abstract.
Grahner, B. et al. (1994). "Synthesis and Structure–Activity Relationships of Deazaxanthines: Analogs of Potent A$_1$– and A$_2$– Adenosine Receptor Antagonists," *J. Med. Chem.* 37:1526–1534.
Gristwood, R. W. et al. (1992). "Studies On The Cardiac Actions of Flosequinan in vitro," *Br. J. Pharmacol.* 105:985–991.

Noell, C. W. and Robins, R. K. (Feb. 1964). "Aromaticity in Heterocyclic Systems. II. The Application of N.M.R. in a Study of the Synthesis and Structure of Certain Imidazo [1.2–c] Pyrimidines and Related Pyrrolo [2,3–d] Pyrimidines," *J. Heterocycl. Chem.* Vol. 1, pp. 34–41.
Ogura, H. et al., (1972). "Synthesis of Pyrrolopyrimidines and Thienopyrimidines," *Chem. Pharm. Bull.* 20(2):404–408.
Papesh, V. and Schroeder, E. F. (1951). "Synthesis of 1–mono– and 1,3–di–Substituted 6–Amino–Uracils. Diuretic Activity," *J. Org. Chem.* 16:1879–1890.
H. Cottam et al., Substituted Xanthines, Pteridinediones, And Related Compounds As Potential Antiinflammatory Agents: Synthesis And Biological Evaluaton Of Inhibitors Of Tumor Necrosis Factor α, *J. Med. Chem.* (1996) 39:2–9.
V. Papesch and Elmer F. Schroeder, Synthesis Of 1–Mono– And 1,3–Di–Substituted 6–Amino–Uracils. Diuretic Activity, *J. of Organic Chemistry* (1951), 39:1879–1890.
M. Merlos et al., Structure–Activity Relationships In A Series Of Xanthine Derivatives With Antibronchoconstrictory And Bronchodilatory Activities, *Eur. J. Med. Chem.* (1990) 25:653–658.

* cited by examiner

*Primary Examiner*—Thomas C. McKenzie
(74) *Attorney, Agent, or Firm*—Morrison & Foerster LLP

(57) ABSTRACT

The invention relates to new 6-phenylpyrrolopyrimidine derivatives of formula (I):

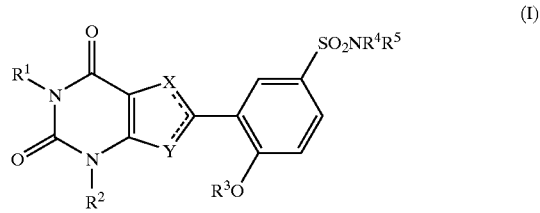

wherein: —X—C—Y— represents

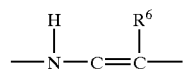

or —X—C—Y— represents

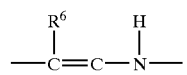

and to their use as selective cyclic GMP specific phosphodiesterase (PDE 5)inhibitors, processes for producing them, intermediates used in their production, compositions containing them and their applicability in medical treatment of the human or animal body.

16 Claims, No Drawings

6-PHENYLPYRROLOPYRIMIDINEDIONE DERIVATIVES

CROSS REFERENCE TO RELATED APPLICATIONS

This application is a continuation of International Application No. PCT/EP01/06306, filed Jun. 1, 2001, and published in Enalish on Dec. 13, 2001, which claims the benefit of Spain Application No. P 200001436, filed Jun. 7, 2000, the contents of each are incorporated herein by reference.

This invention relates to new therapeutically useful pyrrolopyrimidinedione derivatives, to processes for their preparation and to pharmaceutical compositions containing them.

EP Publication No. 0 480 659 A2 relates to compounds of general formula

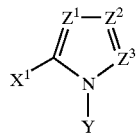

wherein each of $Z^1$, $Z^2$ and $Z^3$ independently represents: a nitrogen atom, a group represented by general formula: $=C(X^2)-$ or a group represented by general formula: $=C(X^3)-$. When $Z^2$ and $Z^3$ represent a group of general formula: $=C(X^2)-$ or a group of general formula: $=C(X^3)-$, $X^2$ and $X^3$ may be combined together to form a group represented by general formula:

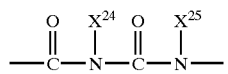

or a group represented by general formula:

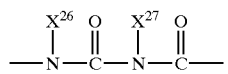

wherein $X^{24}$, $X^{25}$, $X^{26}$ and $X^{27}$ independently represent hydrogen or alkyl of 1 to 4 carbons atoms and Y does not represent hydrogen; which possess angiotensin-II receptor-antagonizing activity for the prevention or treatment of hyperuricemia.

We have now found that certain 6-(disubstituted)phenyl-1,5-dihydropyrrolo[3,2-d]pyrimidine-2,4-dione and 6-(disubstituted)phenyl-1,7-dihydropyrrolo[2,3-d]pyrimidine-2,4-dione derivatives are potent and selective inhibitors of phosphodiesterase 5 (PDE 5), and have efficacy in the treatment of angina, hypertension, congestive heart failure, stroke, asthma, male erectile dysfunction, female sexual dysfunction, premature labour, dysmenorrhea, BPH, incontinence, glaucoma and iritable bowel syndrome.

Accordingly, the present invention provides compounds which are 6-phenylpyrrolopyrimidine derivatives of formula (I):

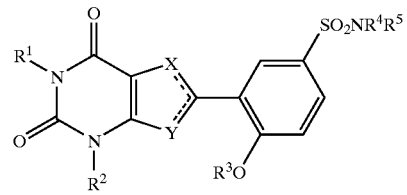

wherein: $-X-C-Y-$ represents

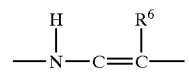

as in formula (II)

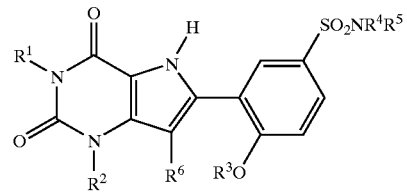

or $-X-C-Y-$ represents

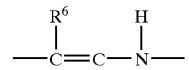

as in formula (III)

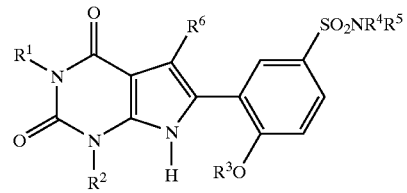

$R^1$, $R^2$ and $R^3$ each independently represent: a hydrogen atom, an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups; or a group of formula

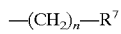

wherein n is an integer from 0 to 4 and $R^7$ represents: a cycloalkyl group; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, phenyl, alkoxycarbonyl, amino, mono-alkylamino, di-alkylamino or hydroxycarbonyl groups or one or more alkyl groups which may in turn be unsubstituted or substituted by one or more halogen atoms or hydroxy, alkoxy, hydroxyalkoxy, phenyl, alkoxycarbonyl, amino, mono- or di-alkylamino or hydroxycarbonyl groups, either R⁴ and R⁵ together with the nitrogen atom to which they are attached form a 3 to 7-membered ring comprising a total of from 1 to 4 heteroatoms selected from nitrogen, oxygen and sulphur, which ring may be unsubstituted or substituted by one or two substituents selected from (a) halogen atoms and hydroxy, oxoalkyl, carbamoyl, hydroxycarbonyl, alkoxycarbonyl, amino, mono- and di-alkylamino groups and (b) alkyl, alkenyl and divalent alkylene groups which may in turn be unsubstituted or substituted by one or more hydroxy, alkoxy, hydroxyalkoxy, amino or mono- or di-alkylamino groups, or R⁴ and R⁵ independently represent a hydrogen atom or an alkyl group which may be unsubstituted or substituted by one or more hydroxy, alkoxy, alkylthio, amino, mono- or di-alkylamino groups, or R⁴ represents a hydrogen atom or an alkyl group and R⁵ represents a group of formula —(CH₂)ₙ—R⁷ as defined above, R⁶ represents a hydrogen or halogen atom, or a nitro or alkoxycarbonyl group, or an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups, or an N-oxide or a pharmaceutically acceptable salt thereof.

The alkyl groups and moieties such as those present in the alkoxy, alkylcarbamoyl, mono- or di-alkylamino, carbamoyl, alkyl, alkylthio, oxoalkyl, alkylenedioxy and alkoxycarbamoyl groups mentioned herein unless otherwise stated are usually "lower" alkyl, that is containing from 1 to 6 particularly from 1 to 4 carbon atoms, the hydrocarbon chain being branched or straight. Preferred alkyl groups, and where relevant alkyl moieties, include methyl, ethyl, n-propyl, i-propyl, n-butyl, sec-butyl and t-butyl.

A said divalent alkylene group is typically a C₁–C₆ alkylene group. Preferably, it is a C₁–C₄ alkylene group, for example a methylene, ethylene or propylene group.

The alkenyl groups and moieties are typically C₂–C₆ alkenyl groups and moieties, for example C₂–C₄ alkenyl groups and moieties.

The halogen atoms mentioned in relation to the groups R⁴ to R⁷ are selected from fluorine, chlorine, bromine and iodine and most preferably from bromine, chlorine and fluorine atoms.

In substituent groups of formula

n may represent 0, 1, 2, 3, or 4, preferably 0, 1, 2 or 3.

The cycloalkyl group mentioned in relation to the group R⁷ is preferably a C₃₋₁₀ cycloalkyl group, more preferably a C₃₋₇ cycloalkyl group such as cyclopropyl, cyclobutyl, cyclopentyl and cyclohexyl group. The cycloalkyl-alkyl groups within the definition —(CH₂)ₙ—R⁷ preferably include cyclopropylmethylene, cyclopropyl-ethylene, cyclopentylmethylene, cyclopentylethylene, cyclohexylmethylene and cyclohexylethylene.

When R⁷ represents a phenyl group substituted by one or more halogen atoms or alkyl, hydroxy, alkoxy, amino, mono- or dialkyl amino, nitro, cyano or trifluoroalkyl groups, the phenyl ring may be substituted by 1, 2, 3, 4 or 5 substituents, preferably 1, 2 or 3 substituents, each being independently selected from the possible substituents set out above. That is to say, the phenyl group (attached through its 1-position) may be substituted at any of the remaining positions, that is to say the 2, 3, 4, 5 or 6-positions. A phenyl group having more than one substituent may be substituted at any combination of positions. For example a phenyl group having two substituents may be substituted at the 2 and 3, 2 and 4, 2 and 5, 2 and 6, 3 and 4 or 3 and 5 positions. If the phenyl group is substituted by one or more alkylene dioxy groups then they may be present on any adjacent pair of substitutable positions.

When R⁷ represents a 3–7 membered ring in accordance with formula (I), the ring may be unsaturated or saturated and may represent for example a piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, triazolyl, tetrazolyl or thienyl group, which group may be substituted or unsubstituted. Typically, the group is unsubstituted or substituted by one or more, for example 1, 2, 3 or 4, substituents selected from C₁–C₄ alkyl groups, for example methyl groups.

In preferred compounds of the invention R¹, R² and R³ each independently represent hydrogen or an unsubstituted alkyl group selected from methyl, ethyl, n-propyl, i-propyl, n-butyl, sec-butyl and t-butyl. In the most preferred compounds of the invention R¹ is a methyl group, R² is an n-propyl or i-butyl group (preferably an n-propyl group), and R³ is an ethyl or n-propyl group.

For compounds of the invention wherein R⁴ and R⁵ together with the nitrogen atom to which they are attached form a ring, the ring may be saturated or unsaturated for example a piperidyl, pyrrolidyl, azetidinyl, aziridyl, piperazinyl, morpholinyl, thiomorpholinyl, pyrrolyl, pyrazolyl, imadazolyl, imadazolidinyl, pyrazolinyl, diazacycloheptyl (diazapanyl), indolinyl or isoindolinyl group, said group being substituted or unsubstituted. Typically, when R⁴ and R⁵, together with the nitrogen atom to which they are attached, form a said 3- to 7-membered ring, the ring is unsubstituted or substituted by one or two halogen atoms or hydroxy, oxoalkyl, carbamoyl, hydroxycarbonyl, alkoxycarbonyl, amino, mono- or di-alkylamino groups or one or two alkyl groups which may in turn be unsubstituted or substituted by one or more hydroxy, alkoxy, hydroxyalkoxy, amino or mono- or di-alkylamino groups.

In one group of preferred compounds of the invention the ring formed by R⁴, R⁵ and the nitrogen atom to which they are attached is a substituted or unsubstituted 4, 5, 6 or 7 membered ring such as a piperidyl, piperazinyl, morpholinyl, diazacycloheptyl, azacyclobutyl, pyrrolidinyl or pyrazolyl group. More typically, in this group of preferred compounds, the ring is a substituted or unsubstituted 5, 6 or 7 membered ring such as a piperidyl, piperazinyl, morpholinyl, diazacycloheptyl, pyrrolidinyl or pyrazolyl group. If the ring is substituted then the substituents are preferably selected from (a) hydroxy, carboxy, alkoxy, carbamoyl, carbaldehyde, alkoxycarbonyl, amino, mono- and di-alkylamino groups and (b) alkyl, alkenyl and divalent alkylene groups having up to 6 C atoms (preferably up to 3 C atoms), which groups may be unsubstituted or substituted by hydroxy, methoxy, hydroxymethoxy or di-alkylamino groups. More typically, the substituents are selected from hydroxy, carboxy, alkoxy, carbamoyl, carbaldehyde, alkoxycarbonyl, amino, mono- or di-alkylamino groups and C₁₋₆, preferably C₁₋₃, alkyl groups which may be unsubstituted or substituted by hydroxy, methoxy, hydroxymethoxy or di-alkylamino groups.

When the ring is substituted by a divalent alkylene group, the divalent alkylene substituent may be attached to adjacent atoms on the ring or to atoms on the ring which are not adjacent. Preferably, when the ring is substituted by a divalent alkylene group it is a piperazinyl group.

Preferably, $R^4$, $R^5$ and the nitrogen atom to which they are attached form a 5, 6 or 7 membered ring comprising a total of from 1 to 3 heteroatoms selected from nitrogen, oxygen or sulphur, which ring may be unsubstituted or substituted by one or more groups selected from hydroxy, carboxy, alkoxy, carbamoyl, carbaldehyde, alkoxycarbonyl, amino, mono- or di-alkylamino groups and alkyl groups which may be unsubstituted or substituted by one or more hydroxy, methoxy, hydroxymethoxy or di-alkylamino groups.

Most preferably the ring is a 4-hydroxypiperidyl, 3-carbamoylpiperidyl, 4-carbamoylpiperidyl, 3-carboxypiperidyl, 4-carboxypiperidyl, 3-ethoxycarbonylpiperidyl, 4-ethoxycarbonylpiperidyl, 4-dimethylaminopiperidyl, 4-(2-dimethylaminoethyl)-4-methylpiperidyl, piperazinyl, 3-methylpiperazinyl, 4-methylpiperazinyl, 2,5-dimethylpiperazinyl, 3,5-dimethylpiperazinyl, 4-ethylpiperazinyl, 4-propylpiperazinyl, 4-hydroxyethylpiperazinyl, 4-methoxy-ethylpiperazinyl, 4-ethoxyethylpiperazinyl, 4-hydroxypropylpiperazinyl, 4-ethoxycarbonylpiperazinyl, 4-ethoxycarbonyl-methylpiperazinyl, 4-propenylpiperazinyl, 4-(2-hydroxyethoxy)ethylpiperazinyl, hexahydropyrrolo[1,2-a]pyrazinyl, 3-methylhexahydropyrrolo[1,2-a]pyrazinyl, 7-hydroxyhexahydropyrrolo[1,2-a]pyrazinyl, 2,5-diazabicyclo[2.2.1]heptanyl, morpholinyl, 4-methyl-1,4-diazacycloheptyl, 4-(2-hydroxyethyl)-1,4-diazacycloheptyl, 3-(dimethylamino)-1-azacyclobutyl, 2-hydroxycarbonylpyrrolidinyl, 4-piperazinecarbaldehyde, 2-methoxycarbonylpyrrolidinyl or aminopyrazolyl group.

Especially preferred are a piperazinyl, 4-methylpiperazinyl, 4-ethyl-piperazinyl, morpholinyl, 4-(2-hydroxyethyl)piperazinyl, 4-(3-hydroxypropyl)piperazinyl, 4-ethoxycarbonyl piperazinyl, 4-methyl-1,4-diazacycloheptyl, 4-(2-methoxyethyl)piperazinyl or 4-piperazinecarbaldehyde group.

In one preferred group of compounds of the invention $R^5$ is a group of formula

—(CH$_2$)$_n$R$^7$ wherein n is 0, 1, 2 or 3 and $R^7$ is a group $R^8$ which represents a substituted or unsubstituted morpholinyl, pyridyl, piperidyl, piperazinyl, quinuclidinyl, triazolyl or tetrazolyl group. Substituents can be, for example, alkyl, hydroxyalkyl, alkoxyalkyl, oxoalkyl, alkoxyalkyl, carbamoyl and alkylcarbamoyl groups.

Most preferably $R^8$ represents an unsubstituted morpholinyl, pyridyl or piperidyl group, a piperidyl group substituted by 1, 2, 3 or 4 methyl groups, or a piperazinyl or quinuclidinyl group substituted at a nitrogen atom by a methyl, ethyl, 2-hydroxyethyl, 2-methoxyethyl, propyl, 3-hydroxypropyl, 3-methoxypropyl, carbaldehyde or ethoxycarbonyl group. More typically, in this preferred embodiment, $R^8$ represents an unsubstituted morpholinyl, pyridyl, piperidyl group or a piperazinyl or quinuclidinyl group substituted at a nitrogen atom by a methyl, ethyl, 2-hydroxyethyl, 2-methoxyethyl, propyl, 3-hydroxypropyl, 3-methoxypropyl, carbaldehyde or ethoxycarbonyl group.

In compounds of the invention wherein $R^4$ and $R^5$ do not form a ring and $R^5$ is not a group of formula
—(CH$_2$)$_n$R$^7$

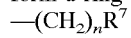

$R^4$ and $R^5$ are preferably independently selected from a hydrogen atom, methyl group, ethyl group or a C$_{1-6}$ alkyl group substituted by one or more halogen atoms or hydroxy, alkoxy, alkylthio, oxo, hydroxycarbonyl, alkoxycarbonyl, carbamoyl, alkylcarbamoyl or mono- or di-alkylamino groups.

In the most preferred compounds of the invention wherein $R^4$ and $R^5$ together do not form a ring, $R^4$ represents a hydrogen atom or a methyl or 2-hydroxyethyl group.

In the most preferred compounds of the invention wherein $R^4$ and $R^5$ together do not form a ring, $R^5$ represents a 2-hydroxyethyl, 2-dimethylaminoethyl, 2-pyridylethyl, N-piperidylethyl, 2,2,6,6-tetramethylpiperidin-4-yl, N-morpholinylethyl, N-morpholinylpropyl or N-methyl-N-piperazinyl group. More typically, in this preferred embodiment, $R^5$ represents a 2-hydroxyethyl, 2-dimethylaminoethyl, 2-pyridylethyl, N-piperidylethyl, N-morpholinylethyl, N-morpholinylpropyl or N-methyl-N-piperazinyl group.

In preferred compounds of the invention $R^6$ represents a hydrogen atom, fluorine atom, chlorine atom, bromine atom, iodine atom or a methyl group which is unsubstituted or substituted by a dimethylamino or methoxy group. More typically, in these preferred compounds, $R^6$ represents a hydrogen atom, fluorine atom, chlorine atom or a methyl group.

In compounds of the invention wherein —X—C—Y— represents

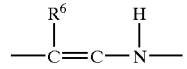

(as in formula (III) above) $R^6$ preferably represents a hydrogen atom or a dialkylaminoalkyl group.

Particular individual compounds of the invention include:
6-[2-Ethoxy-5-(4-methylpiperazine-1-sulphonyl)phenyl]-3-methyl-1-propyl-1,5-dihydropyrrolo[3,2-d]pyrimidine-2,4-dione 6-[2-Ethoxy-5-(piperazine-1-sulfonyl)phenyl]-3-methyl-1-propyl-1,5-dihydropyrrolo[3,2-d]pyrimidine-2,4-dione 6-[2-Ethoxy-5-(morpholine-4-sulfonyl)phenyl]-3-methyl-1-propyl-1,5-dihydropyrrolo[3,2-d]pyrimidine-2,4-dione N-(2-Dimethylaminoethyl)-4-ethoxy-3-(methyldioxopropyl-2,3,4,5-tetrahydro-1H-pyrrolo[3,2-d]pyrimidin-6-yl)benzene sulfonamide 6-[2-Ethoxy-5-(4-ethylpiperazine-1-sulfonyl)phenyl]-3-methyl-1-propyl-1,5-dihydropyrrolo[3,2-d]pyrimidine-2,4-dione 6-[2-Ethoxy-5-(4-methyl-[1,4]diazepane-1-sulfonyl)phenyl]-3-methyl-1-propyl-1,5-dihydropyrrolo[3,2-d]pyrimidine-2,4-dione 4-Ethoxy-3-(3-methyl-2,4-dioxo-1-propyl-2,3,4,5-tetrahydro-1H-pyrrolo[3,2-d]pyrimidin-6-yl)-N-(2-piperidin-1-yl-ethyl)benzenesulfonamide 4-Ethoxy-3-(3-methyl-2,4-dioxo-1-propyl-2,3,4,5-tetrahydro-1H-pyrrolo[3,2-d]pyrimidin-6-yl)-N-(2-morpholin-4-yl-ethyl)benzenesulfonamide 6-{2-Ethoxy-5-[4-(2-hydroxyethyl)piperazine-1-sulfonyl]phenyl}-3-methyl-1-propyl-1,5-dihydropyrrolo[3,2-d]pyrimidine-2,4-dione 4-Ethoxy-3-(3-methyl-2,4-dioxo-1-propyl-2,3,4,5-tetrahydro-1H-pyrrolo[3,2-d]pyrimidin-6-yl)-N-(3-morpholin-4-yl-propyl)benzenesulfonamide 6-{2-Ethoxy-5-[4-(3-hydroxypropyl)piperazine-1-sulfonyl]phenyl}-3-methyl-1-propyl-1,5-dihydropyrrolo[3,2-d]pyrimidine-2,4-dione 3-Methyl-6-[5-(4-methylpiperazine-1-sulphonyl)-2-propoxyphenyl]-1-propyl-1,5-dihydropyrrolo[3,2-d]pyrimidine-2,4-dione 6-[5-(4-Ethylpiperazine-1-sulphonyl)-2-propoxyphenyl]-3-methyl-1-propyl-1,5-dihydropyrrolo[3,2-d]pyrimidine-2,4-dione 6-{5-[4-(2-Hydroxyethyl)piperazine-1-sulphonyl]-2-propoxyphenyl}-3-methyl-1-propyl-1,5-dihydropyrrolo[3,2-d]pyrimidine-2,4-dione 3-Methyl-6-[5-(piperazine-1-sulfonyl)-2-propoxyphenyl]-1-propyl-1,5-dihydropyrrolo[3,2-d]pyrimidine-2,4-dione 3-Methyl-6-[5-(morpholine-4-sulfonyl)-2-propoxyphenyl]-1-propyl-1,5-dihydropyrrolo[3,2-d]pyrimidine-2,4-dione N-(2-Dimethylaminoethyl)-3-(methyldioxopropyl-2,3,4,5-tetrahydro-1H-pyrrolo[3,2-d]pyrimidin-6-yl)-4-propoxybenzenesulfonamide N,N-Bis-(2-hydroxyethyl)-3-(3-methyl-2,4-dioxo-1-propyl-2,3,4,5-tetrahydro-1H-pyrrolo[3,2-d]pyrimidin-6-yl)-4-propoxybenzenesulfonamide 3-Methyl-6-[5-(4-methyl-[1,4]diazepane-1-sulfonyl)-2-propoxyphenyl]-1-propyl-1,5-dihydropyrrolo[3,2-d]pyrimidine-2,4-dione 3-(3-Methyl-2,4-dioxo-1-propyl-2,3,4,5-tetrahydro-1H-pyrrolo[3,2-d]pyrimidin-6-yl)-N-(4-methylpiperazin-1-yl)-4-propoxybenzenesulfonamide 3-(3-Methyl-2,4-dioxo-1-propyl-2,3,4,5-tetrahydro-1H-pyrrolo[3,2-d]pyrimidin-6-yl)-4-propoxy-N-(2-pyridin-2-yl-ethyl)benzenesulfonamide 3-(3-Methyl-2,4-dioxo-1-propyl-2,3,4,5-tetrahydro-1H-pyrrolo[3,2-d]pyrimidin-6-yl)-N-(2-piperidin-1-ylethyl-4-propoxybenzenesulfonamide 3-(3-Methyl-2,4-dioxo-1-propyl-2,3,4,5-tetrahydro-1H-pyrrolo[3,2-d]pyrimidin-6-yl)-N-(2-morpholin-4-yl-ethyl)-4-propoxybenzenesulfonamide 3-(3-Methyl-2,4-dioxo-1-propyl-2,3,4,5-tetrahydro-1H-pyrrolo[3,2-d]pyrimidin-6-yl)-N-(3-morpholin-4-ylpropyl)-4-propoxybenzenesulfonamide 6-{5-[4-(3-Hydroxypropyl)piperazine-1-sulfonyl]-2-propoxyphenyl}-3-methyl-1-propyl-1,5-dihydropyrrolo[3,2-d]pyrimidine-2,4-dione 7-Chloro-6-[2-ethoxy-5-(piperazine-1-sulfonyl)phenyl]-3-methyl-1-propyl-1,5-dihydropyrrolo[3,2-d]pyrimidine-2,4-dione 7-Chloro-6-[2-ethoxy-5-(4-methylpiperazine-1-sulfonyl)phenyl]-3-methyl-1-propyl-1,5-dihydropyrrolo[3,2-d]pyrimidine-2,4-dione 7-Chloro-6-[2-ethoxy-5-(4-ethylpiperazine-1-sulfonyl)phenyl]-3-methyl-1-propyl-1,5-dihydropyrrolo[3,2-d]pyrimidine-2,4-dione 7-Chloro-6-{2-ethoxy-5-[4-(2-hydroxyethyl)piperazine-1-sulfonyl]phenyl}-3-methyl-1-propyl-1,5-dihydropyrrolo[3,2-d]pyrimidine-2,4-dione 3-(Chloromethyldioxopropyl-2,3,4,5-tetrahydro-1H-pyrrolo[3,2-d]pyrimidin-6-yl)-N-(2-dimethylaminoethyl)-4-ethoxybenzenesulfonamide 7-Chloro-6-[2-ethoxy-5-(4-methyl-[1,4]diazepane-1-sulfonyl)phenyl]-3-methyl-1-propyl-1,5-dihydropyrrolo[3,2-d]pyrimidine-2,4-dione 3-(7-Chloro-3-methyl-2,4-dioxo-1-propyl-2,3,4,5-tetrahydro-1H-pyrrolo[3,2-d]pyrimidin-6-yl)-4-ethoxy-N-(2-morpholin-4-ylethyl)benzenesulfonamide 7-Chloro-3-methyl-6-[5-(4-methylpiperazine-1-sulfonyl)-2-propoxyphenyl]-1-propyl-1,5-dihydropyrrolo[3,2-d]pyrimidine-2,4-dione 7-Chloro-6-[5-(4-ethylpiperazine-1-sulfonyl)-2-propoxyphenyl]-3-methyl-1-propyl-1,5-dihydropyrrolo[3,2-d]pyrimidine-2,4-dione 7-Chloro-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione 7-Bromo-6-[2-ethoxy-5-(morpholine-4-sulfonyl)phenyl]-3-methyl-1-propyl-1,5-dihydropyrrolo[3,2-d]pyrimidine-2,4-dione 7-Bromo-6-[2-ethoxy-5-(4-methylpiperazine-1-sulfonyl)phenyl]-3-methyl-1-propyl-1,5-dihydropyrrolo[3,2-d]pyrimidine-2,4-dione 4-[3-(7-Bromo-3-methyl-2,4-dioxo-1-propyl-2,3,4,5-tetrahydro-1H-pyrrolo[3,2-d]pyrimidin-6-yl)-4-ethoxybenzenesulfonyl]piperazine-1-carbaldehyde 7-Bromo-6-[2-ethoxy-5-(4-ethylpiperazine-1-sulfonyl)phenyl]-3-methyl-1-propyl-1,5-dihydropyrrolo[3,2-d]pyrimidine-2,4-dione 7-Bromo-6-[2-ethoxy-5-(4-methyl-[1,4]diazepane-1-sulfonyl)phenyl]-3-methyl-1-propyl-1,5-dihydropyrrolo[3,2-d]pyrimidine-2,4-dione 3-(7-Bromo-3-methyl-2,4-dioxo-1-propyl-2,3,4,5-tetrahydro-1H-pyrrolo[3,2-d]pyrimidin-6-yl)-4-ethoxy-N-(4-methylpiperazin-1-yl)benzenesulfonamide 3-(7-Bromo-3-methyl-2,4-dioxo-1-propyl-2,3,4,5-tetrahydro-1H-pyrrolo[3,2-d]pyrimidin-6-yl)-4-ethoxy-N-(2-pyridin-2-ylethyl)benzenesulfonamide 3-(7-Bromo-3-methyl-2,4-dioxo-1-propyl-2,3,4,5-tetrahydro-1H-pyrrolo[3,2-d]pyrimidin-6-yl)-4-ethoxy-N-(2-piperidin-1-ylethyl)benzenesulfonamide 7-Bromo-6-{2-ethoxy-5-[4-(2-hydroxyethyl)piperazine-1-sulfonyl]phenyl}-3-methyl-1-propyl-1,5-dihydropyrrolo[3,2-d]pyrimidine-2,4-dione 3-(7-Bromo-3-methyl-2,4-dioxo-1-propyl-2,3,4,5-tetrahydro-1H-pyrrolo[3,2-d]pyrimidin-6-yl)-4-ethoxy-N-(2-morpholin-4-ylethyl)benzenesulfonamide 3-(7-Bromo-3-methyl-2,4-dioxo-1-propyl-2,3,4,5-tetrahydro-1H-pyrrolo[3,2-d]pyrimidin-6-yl)-4-ethoxy-N-(3-morpholin-4-ylpropyl)benzenesulfonamide 7-Bromo-6-{2-ethoxy-5-[4-(3-hydroxypropyl)piperazine-1-sulfonyl]phenyl}-3-methyl-1-propyl-1,5-dihydropyrrolo[3,2-d]pyrimidine-2,4-dione 7-Bromo-6-{2-ethoxy-5-[4-(2-methoxyethyl)piperazine-1-sulfonyl]phenyl}-3-methyl-1-propyl-1,5-dihydropyrrolo[3,2-d]pyrimidine-2,4-dione 7-Bromo-3-methyl-6-[5-(morpholine-4-sulfonyl)-2-propoxyphenyl]-1-propyl-1,5-dihydropyrrolo[3,2-d]pyrimidine-2,4-dione 7-Bromo-3-methyl-6-[5-(4-methylpiperazine-1-sulfonyl)-2-propoxyphenyl]-1-propyl-1,5-dihydropyrrolo[3,2-d]pyrimidine-2,4-dione 4-[3-(7-Bromo-3-methyl-2,4-dioxo-1-propyl-2,3,4,5-tetrahydro-1H-pyrrolo[3,2-d]pyrimidin-6-yl)-4-propoxybenzenesulfonyl]piperazine-1-carbaldehyde 7-Bromo-6-[5-(4-ethylpiperazine-1-sulfonyl)-2-propoxyphenyl]-3-methyl-1-propyl-1,5-dihydro-pyrrolo[3,2-d]pyrimidine-2,4-dione 7-Bromo-3-methyl-6-[5-(4-methyl-[1,4]diazepane-1-sulfonyl)-2-propoxyphenyl]-1-propyl-1,5-dihydro-pyrrolo[3,2-d]pyrimidine-2,4-dione 3-(7-Bromo-3-methyl-2,4-dioxo-1-propyl-2,3,4,5-tetrahydro-1H-pyrrolo[3,2-d]pyrimidin-6-yl)-N-(2-morpholin-4-ylethyl)-4-propoxybenzenesulfonamide 7-Bromo-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione 3-(7-Bromo-3-methyl-2,4-dioxo-1-propyl-2,3,4,5-tetrahydro-1H-pyrrolo[3,2-d]pyrimidin-6-yl)-N-(3-morpholin-4-ylpropyl)-4-propoxybenzenesulfonamide 7-Bromo-6-{5-[4-(3-hydroxypropyl)piperazine-1-sulfonyl]-2-propoxyphenyl}-3-methyl-1-propyl-1,5-dihydropyrrolo[3,2-d]pyrimidine-2,4-dione 7-Chloro-6-[2-ethoxy-5-(4-methylpiperazine-1-sulfonyl)phenyl]-1-isobutyl-3-methyl-1,5-dihydropyrrolo[3,2-d]pyrimidine-2,4-dione 7-Chloro-6-[2-ethoxy-5-(4-ethylpiperazine-1-sulfonyl) phenyl]-1-isobutyl-3-methyl-1,5-dihydropyrrolo[3,2-d] pyrimidine-2,4-dione 7-Chloro-6-{2-ethoxy-5-[4-(2-hydroxyethyl)piperazine-1-sulfonyl]phenyl}-1-isobutyl-3-methyl-1,5-dihydropyrrolo[3,2-d]pyrimidine-2,4-dione 7-Chloro-6-[2-ethoxy-5-(piperazine-1-sulfonyl)phenyl]-1-isobutyl-3-methyl-1,5-dihydropyrrolo[3,2-d]pyrimidine-2,4-dione 7-Chloro-6-[2-ethoxy-5-(4-methyl-4-oxypiperazine-1-sulfonyl)phenyl]-3-methyl-1-propyl-1,5-dihydropyrrolo[3,2-d]pyrimidine-2,4-dione 3-(7-Chloro-3-methyl-2,4-dioxo-1-propyl-2,3,4,5-tetrahydro-1H-pyrrolo[3,2-d]pyrimidin-6-yl)-4-ethoxy-N-(2-methylaminoethyl)benzenesulfonamide 7-Chloro-6-{2-ethoxy-5-[4-(3-hydroxypropyl) piperazine-1-sulfonyl]phenyl}-3-methyl-1-propyl-1,5-dihydropyrrolo[3,2-d]pyrimidine-2,4-dione 3-(7-Chloro-3-methyl-2,4-dioxo-1-propyl-2,3,4,5-tetrahydro-1H-pyrrolo[3,2-d]pyrimidin-6-yl)-4-ethoxy-N-(2-pyridin-2-ylethyl)benzenesulfonamide 7-Chloro-6-{2-ethoxy-5-[4-(2-ethoxyethyl)piperazine-1-sulfonyl]phenyl}-3-methyl-1-propyl-1,5-dihydropyrrolo[3,2-d]pyrimidine-2,4-dione 6-[5-(4-Allylpiperazine-1-sulfonyl)-2-ethoxyphenyl]-7-chloro-3-methyl-1-propyl-1,5-dihydropyrrolo[3,2-d] pyrimidine-2,4-dione 7-Chloro-6-[2-ethoxy-5-(4-isopropylpiperazine-1-sulfonyl)phenyl]-3-methyl-1-propyl-1,5-dihydropyrrolo[3,2-d]pyrimidine-2,4-dione 7-Chloro-6-{2-ethoxy-5-[(S)-(hexahydropyrrolo[1,2-a] pyrazin-2-yl)sulfonyl]-phenyl}-3-methyl-1-propyl-1,5-dihydropyrrolo[3,2-d]pyrimidine-2,4-dione 7-Chloro-6-{2-ethoxy-5-[(R)-(hexahydropyrrolo[1,2-a] pyrazin-2-yl)sulfonyl]-phenyl}-3-methyl-1-propyl-1,5-dihydropyrrolo[3,2-d]pyrimidine-2,4-dione 7-Chloro-6-[2-ethoxy-5-((3R,8aS)-3-methylhexahydropyrrolo[1,2-a]pyrazine-2-sulfonyl) phenyl]-3-methyl-1-propyl-1,5-dihydropyrrolo[3,2-d] pyrimidine-2,4-dione 7-Chloro-6-[2-ethoxy-5-((7R,8aS)-7-hydroxyhexahydropyrrolo[1,2-a]pyrazine-2-sulfonyl) phenyl]-3-methyl-1-propyl-1,5-dihydropyrrolo[3,2-d] pyrimidine-2,4-dione 7-Chloro-6-[2-ethoxy-5-((1S,4S)-5-methyl-2,5-diazabicyclo[2.2.1]heptane-2-sulfonyl)phenyl]-3-methyl-1-propyl-1,5-dihydropyrrolo[3,2-d]pyrimidine-2,4-dione 6-[2-Ethoxy-5-(4-methylpiperazine-1-sulfonyl)phenyl]-7-iodo-3-methyl-1-propyl-1,5-dihydropyrrolo[3,2-d] pyrimidine-2,4-dione 6-[5-(3-Dimethylaminoazetidine-1-sulfonyl)-2-ethoxyphenyl]-7-iodo-3-methyl-1-propyl-1,5-dihydropyrrolo[3,2-d]pyrimidine-2,4-dione 6-[2-Ethoxy-5-(4-methyl-[1,4]diazepane-1-sulfonyl) phenyl]-7-iodo-3-methyl-1-propyl-1,5-dihydropyrrolo[3,2-d]pyrimidine-2,4-dione 6-[2-Ethoxy-5-(4-ethylpiperazine-1-sulfonyl)phenyl]-7-iodo-3-methyl-1-propyl-1,5-dihydropyrrolo[3,2-d] pyrimidine-2,4-dione 6-[5-(4-Allylpiperazine-1-sulfonyl)-2-ethoxyphenyl]-7-iodo-3-methyl-1-propyl-1,5-dihydropyrrolo[3,2-d] pyrimidine-2,4-dione 6-[2-Ethoxy-5-(4-isopropylpiperazine-1-sulfonyl) phenyl]-7-iodo-3-methyl-1-propyl-1,5-dihydropyrrolo[3,2-d]pyrimidine-2,4-dione 6-{2-Ethoxy-5-[4-(2-hydroxyethyl)piperazine-1-sulfonyl]phenyl}-7-iodo-3-methyl-1-propyl-1,5-dihydropyrrolo[3,2-d]pyrimidine-2,4-dione 6-{2-Ethoxy-5-[4-(2-methoxyethyl)piperazine-1-sulfonyl]phenyl}-7-iodo-3-methyl-1-propyl-1,5-dihydropyrrolo[3,2-d]pyrimidine-2,4-dione 6-[2-Ethoxy-5-(piperazine-1-sulfonyl)phenyl]-7-iodo-3-methyl-1-propyl-1,5-dihydropyrrolo[3,2-d]pyrimidine-2,4-dione 4-Ethoxy-3-(7-iodo-3-methyl-2,4-dioxo-1-propyl-2,3,4,5-tetrahydro-1H-pyrrolo[3,2-d]pyrimidin-6-yl)-N-(2,2,6,6-tetramethylpiperidin-4-yl)benzenesulfonamide 6-{2-Ethoxy-5-[4-(2-hydroxyethyl)[1,4]diazepane-1-sulfonyl]phenyl}-7-iodo-3-methyl-1-propyl-1,5-dihydropyrrolo[3,2-d]pyrimidine-2,4-dione 6-[2-Ethoxy-5-((1S,4S)-5-methyl-2,5-diazabicyclo[2.2.1] heptane-2-sulfonyl)phenyl]-7-iodo-3-methyl-1-propyl-1,5-dihydropyrrolo[3,2-d]pyrimidine-2,4-dione 4-[3-(3-Methyl-2,4-dioxo-1-propyl-2,3,4,7-tetrahydro-1H-pyrrolo[2,3-d]pyrimidin-6-yl)-4-propoxybenzenesulfonyl]piperazine-1-carboxylic acid ethyl ester 3-Methyl-6-[5-(piperazine-1-sulfonyl)-2-propoxyphenyl]-1-propyl-1,7-dihydropyrrolo[2,3-d] pyrimidine-2,4-dione 3-Methyl-6-[5-(morpholine-4-sulfonyl)-2-propoxyphenyl]-1-propyl-1,7-dihydropyrrolo[2,3-d] pyrimidine-2,4-dione 3-Methyl-6-[5-(4-methylpiperazine-1-sulfonyl)-2-propoxyphenyl]-1-propyl-1,7-dihydropyrrolo[2,3-d] pyrimidine-2,4-dione 5-Dimethylaminomethyl-3-methyl-6-[5-(4-methylpiperazine-1-sulfonyl)-2-propoxyphenyl]-1-propyl-1,7-dihydropyrrolo[2,3-d]pyrimidine-2,4-dione 3-Methyl-6-[2-propoxy-5-(4-propylpiperazine-1-sulfonyl)phenyl]-1-propyl-1,7-dihydropyrrolo[2,3-d] pyrimidine-2,4-dione 4-[3-(5-Dimethylaminomethyl-3-methyl-2,4-dioxo-1-propyl-2,3,4,7-tetrahydro-1H-pyrrolo[2,3-d]pyrimidin-6-yl)-4-propoxybenzenesulfonyl]piperazine-1-carboxylic acid ethyl ester 5-Dimethylaminomethyl-3-methyl-6-[5-(morpholine-4-sulfonyl)-2-propoxyphenyl]-1-propyl-1,7-dihydropyrrolo[2,3-d]pyrimidine-2,4-dione 4-[3-(5-Methoxymethyl-3-methyl-2,4-dioxo-1-propyl-2,3,4,7-tetrahydro-1H-pyrrolo[2,3-d]pyrimidin-6-yl)-4-propoxybenzenesulfonyl]piperazine-1-carboxylic acid ethyl ester Of outstanding interest are:

3-Methyl-6-[5-(4-methylpiperazine-1-sulphonyl)-2-propoxyphenyl]-1-propyl-1,5-dihydropyrrolo[3,2-d] pyrimidine-2,4-dione 6-[5-(4-Ethylpiperazine-1-sulphonyl)-2-propoxyphenyl]-3-methyl-1-propyl-1,5-dihydropyrrolo[3,2-d]pyrimidine-2,4-dione 7-Chloro-6-[2-ethoxy-5-(4-methylpiperazine-1-sulfonyl) phenyl]-3-methyl-1-propyl-1,5-dihydropyrrolo[3,2-d] pyrimidine-2,4-dione 7-Chloro-3-methyl-6-[5-(4-methylpiperazine-1-sulfonyl)-2-propoxyphenyl]-1-propyl-1,5-dihydropyrrolo[3,2-d]pyrimidine-2,4-dione 7-Chloro-6-[5-(4-ethylpiperazine-1-sulfonyl)-2-propoxyphenyl]-3-methyl-1-propyl-1,5-dihydropyrrolo[3,2-d]pyrimidine-2,4-dione 7-Chloro-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione 7-Bromo-6-{2-ethoxy-5-[4-(3-hydroxypropyl) piperazine-1-sulfonyl]phenyl}-3-methyl-1-propyl-1,5-dihydropyrrolo[3,2-d]pyrimidine-2,4-dione 7-Bromo-3-methyl-6-[5-(4-methylpiperazine-1-sulfonyl)-2-propoxyphenyl]-1-propyl-1,5-dihydropyrrolo[3,2-d]pyrimidine-2,4-dione 7-Bromo-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione 7-Bromo-6-{5-[4-(3-hydroxypropyl)piperazine-1-sulfonyl]-2-propoxyphenyl}-3-methyl-1-propyl-1,5-dihydropyrrolo[3,2-d]pyrimidine-2,4-dione.

According to a further feature of the present invention, the 6-phenyl-1,5-dihydropyrrolo[3,2-d]pyrimidine-2,4-dione derivatives of general formula (II) are prepared by reaction of the corresponding sulphonyl chloride of formula (IV):

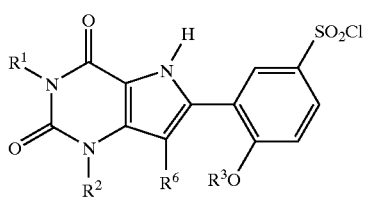
(IV)

(wherein $R^1$, $R^2$, $R^3$ and $R^6$ are as hereinbefore defined) and the corresponding amine (V):

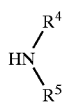
(V)

(wherein $R^4$ and $R^5$ are as hereinbefore defined). The reaction is carried out in an organic solvent, preferably a polar aprotic organic solvent such as dioxane, methylene chloride or tetrahydrofuran, at a temperature from 10° C. to 40° C. and in the presence of an organic base, preferably an amine base such as triethylamine or polymer supported morpholine. The thus obtained 6-phenyl-1,5-dihydropyrrolo[3,2-d]pyrimidine-2,4-dione derivative is then isolated by the usual method known in the art.

In the case that $R^6$ is hydrogen, the sulphonyl chloride (IV) is obtained from the corresponding compound of formula (VI):

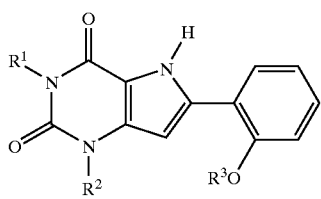
(VI)

(wherein $R^1$, $R^2$ and $R^3$ are as hereinbefore defined), by reaction with an excess of chlorosulphonic acid and optionally thionyl chloride, preferably under a nitrogen atmosphere and at a temperature from −5° C. to 10° C. and where the solvent is the same chlorosulphonic acid.

In the case that $R^6$ is a chlorine atom, the corresponding sulphonyl chloride (IV) is obtained from the corresponding compound of formula (VI) by reaction with an mixture of chlorosulphonic acid and sulphuryl chloride, preferably under a nitrogen atmosphere and at a temperature from −5° C. to 10° C. and where the solvent is the same chlorosulphonic acid.

In the case that $R^6$ is a bromine atom, the desired sulphonyl chloride (IV) is obtained from the corresponding sulphonyl chloride (IV) where $R^6$ is a hydrogen atom by reaction with bromine in glacial acetic acid at room temperature.

Other substitutions at $R^6$ can be introduced by reaction of the corresponding compound of general formula (VI), (IV) or (II, $R^6$=H) or a protected version of them, with an appropiate electrophile.

The 6-phenyl-1,5-dihydropyrrolo[3,2-d]pyrimidine-2,4-dione derivatives of general formula (VI) can be prepared by reaction of the corresponding 6-methyl-5-nitrouracils (VII):

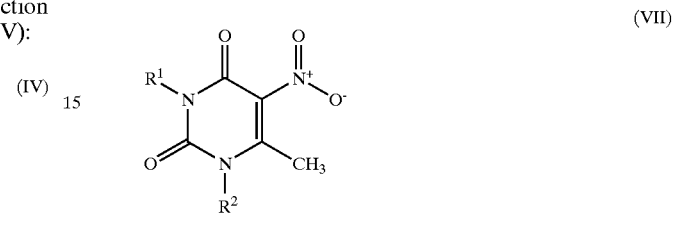
(VII)

(wherein $R^1$ and $R^2$ are as hereinbefore defined), and the corresponding benzaldehydes (VIII):

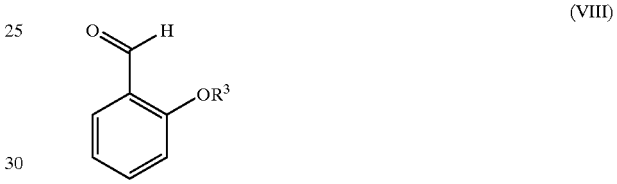
(VIII)

(wherein $R^3$ is as hereinbefore defined), followed by reductive cyclization of the resulting 5-nitro-6-styryluracils by methods known per se, e.g. B. Grahner et al., *J. Med. Chem.* 1994, 37:1526–1534 and references cited therein.

According to a further feature of the present invention, the 6-phenyl-1,7-dihydropyrrolo[2,3-d]pyrimidine-2,4-dione derivatives of general formula (III) are prepared by condensation of the corresponding 6-aminouracil of formula (IX):

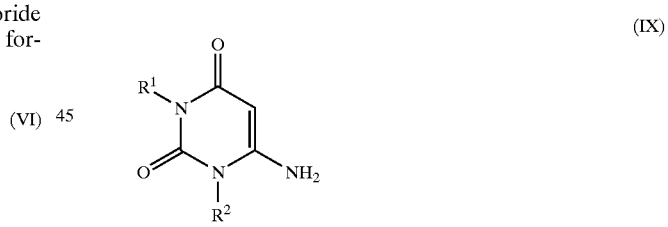
(IX)

(wherein $R^1$ and $R^2$ are as hereinbefore defined), with the corresponding bromoacetophenones of formula (X):

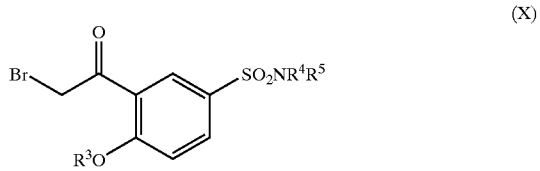
(X)

(wherein $R^3$, $R^4$ and $R^5$ are as hereinbefore defined), by methods known per se, e.g. C. W. Noell et al., *J. Heterocycl. Chem.* 1964, 1:34–41, and H. Ogura et al., *Chem. Pharm. Bull.* 1972, 6:404–408.

Other substitutions at $R^6$ can be introduced by subsequent reaction of the corresponding compound of general formula (III) or a protected version of it, with the corresponding electrophile, as in Example 90. When $R^6$ is a dimethylaminomethyl group, substitution of the dimethylamino moiety by nucleophiles can take place by reaction in the presence of methyl iodide.

The 6-aminouracils of general formula (IX) can be prepared from the corresponding N,N'-disubstituted ureas by methods known per se, e.g. V. Papesch et al., *J. Org. Chem.* 1951, 16:1879–1890.

The bromoacetophenones (X) can be prepared from the corresponding 2-alkoxyacetophenones (XI):

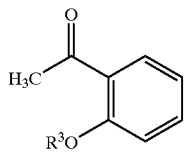

(XI)

(wherein R3 is as hereinbefore defined), by chlorosulphonylation, reaction with the corresponding amine (V):

(V)

and further bromination of the resulting compound by methods known per se.

The 2-alkoxyacetophenones of general formula (XI) can be prepared from 2-hydroxyacetophenone by methods known per se, e.g. M. Covello et al., Farmaco, *Sci. Ed.* 1964, 19:675.

When the defined groups $R^1$ to $R^5$ are susceptible to chemical reaction under the conditions of the hereinbefore described processes or are incompatible with said processes, alternative processes can be readily carried out utilising organic synthetic chemistry methods to, for example, protect functional groups and finally eliminate protecting groups.

The 6-phenyl-1,5-dihydropyrrolo[3,2-d]pyrimidine-2,4-dione and 6-phenyl-1,7-dihydropyrrolo[2,3-d]pyrimidine-2,4-dione derivatives of formula (I) can be converted by methods known per se into pharmaceutically acceptable salts or N-oxides. Preferred salts are acid addition salts obtainable by treatment with organic or inorganic acids such as fumaric, tartaric, succinic or hydrochloric acid. Also 6-phenyl-1,5-dihydropyrrolo[3,2-d]pyrimidine-2,4-dione and 6-phenyl-1,7-dihydropyrrolo[2,3-d]pyrimidine-2,4-dione derivatives of formula (I) in which there is the presence of an acidic group may be converted into pharmacologically acceptable salts by reaction with an alkali metal hydroxide or an organic base such as sodium or potassium hydroxide. The acid or alkali addition salts so formed may be interchanged with suitable pharmaceutically acceptable counter ions using processes known per se.

When the compound of the invention is an N-oxide, the N-oxide group is preferably in the moiety $NR^4R^5$. Preferably, when the compound of the invention is an N-oxide, the moiety $NR^4R^5$ is a piperazinyl group and the N-oxide is present at the 4-N atom.

The cyclic GMP specific phosphodiesterase (PDE 5) was isolated from human platelet lysates by ion exchange chromatography using a Mono-Q column. The enzyme activity was determined using 0.25 mM [3H]-cyclic GMP as substrate. The purification of the enzyme and the assessment of the PDE 5 inhibitory activity of our compounds were performed essentially as described by R. W. Gristwood et al., Br. *J. Pharmacol.* 1992, 105:985–991.

The results are shown in Table 1.

TABLE 1

| Example | $IC_{50}$ PDE5 (nM) |
|---------|---------------------|
| 12      | 14                  |
| 13      | 8                   |
| 27      | 3.4                 |
| 33      | 4.2                 |
| 34      | 3.6                 |
| 35      | 3.4                 |
| 47      | 9.2                 |
| 50      | 4.5                 |
| 55      | 6.6                 |
| 57      | 4                   |

It can be seen from Table 1 that the compounds of formula (I) are potent inhibitors of cyclic GMP specific phosphodiesterase (PDE 5). Preferred 6-phenyl-1,5-dihydropyrrolo[3,2-d]pyrimidine-2,4-dione and 6-phenyl-1,7-dihydropyrrolo[2,3-d]pyrimidine-2,4-dione derivatives of the invention possess an $IC_{50}$ value for the inhibition of PDE 5 (determined as defined above) of less than 30 nM, preferably less than 15 nM and most preferably less than 10 nM. The 6-phenyl-1,5-dihydropyrrolo[3,2-d]pyrimidine-2,4-dione and 6-phenyl-1,7-dihydropyrrolo[2,3-d]pyrimidine-2,4-dione derivatives of the invention are useful in the treatment, including preventative treatment, of any disease or condition which is mediated by or associated with cyclic GMP specific phosphodiesterase (PDE 5) activity including stable, unstable and variant angina, hypertension, pulmonary hypertension, congestive heart failure, renal failure, atherosclerosis, conditions of reduced blood vessel potency, peripheral vascular disease, vascular disorders (e.g. Raynaud's disease), stroke, bronchitis, chronic asthma, allergic asthma, allergic rhinitis, glaucoma, male erectile dysfunction, female sexual dysfunction and diseases characterised by disorders of gut motility, e.g. irritable bowel syndrome.

In addition to their principle activity (the inhibition of cyclic GMP specific phosphodiesterase (PDE 5)) the compounds of the invention may also show activity in the inhibition of other phosphodiesterases, in particular phosphodiesterases 1 and 2, thus having a synergistic effect in raising cyclic nucleotide levels.

Accordingly, the 6-phenyl-1,5-dihydropyrrolo[3,2-d]pyrimidine-2,4-dione and 6-phenyl-1,7-dihydropyrrolo[2,3-d]pyrimidine-2,4-dione derivatives of the invention and pharmaceutically acceptable salts thereof, and pharmaceutical compositions comprising such compound and/or salts thereof, may be used in a method of treatment of disorders of the human body which comprises administering to a patient requiring such treatment an effective amount of a 6-phenyl-1,5-dihydropyrrolo[3,2-d]pyrimidine-2,4-dione and 6-phenyl-1,7-dihydropyrrolo[2,3-d]pyrimidine-2,4-dione derivative of the invention or a pharmaceutically acceptable salt thereof.

The present invention also provides pharmaceutical compositions which comprise, as an active ingredient, at least a 6-phenyl-1,5-dihydropyrrolo[3,2-d]pyrimidine-2,4-dione and 6-phenyl-1,7-dihydropyrrolo[2,3-d]pyrimidine-2,4-dione derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10–600 mg of active ingredient per day. Daily dosage may be administered in one or more treatments, preferably from 1 to 4 treatments, per day.

The syntheses of the compounds of the invention and of the intermediates for use therein are illustrated by the following Examples (including Preparation Examples (Preparations 1–16)) which do not limit the scope of the invention in any way.

$^1$H Nuclear Magnetic Resonance Spectra were recorded on a Varian Gemini 300 spectrometer. Low Resolution Mass Spectra (m/z) were recorded on a Micromass ZMD mass spectrometer using ESI ionization. Melting points were recorded using a Perkin Elmer DSC-7 apparatus. The chromatographic separations were obtained using a Waters 2690 system equipped with a Symmetry C18 (2.1×10 mm, 3.5 mM) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 20 min, and then 4 min. with 95% of B. The reequilibration time between two injections was 5 min. The flow rate was 0.4 mL/min. The injection volume was 5 μL. Diode array chromatograms were collected at 210 nM.

PREPARATION EXAMPLES

Preparation 1

6-(2-Ethoxyphenyl)-3-methyl-1-propyl-1,5-dihydropyrrolo[3,2-d]pyrimidine-2,4-dione a) A mixture of 3,6-dimethyl-5-nitro-1-propyl-1H-pyrimidine-2,4-dione (6.25 g, 27.5 mmol), 2-ethoxybenzaldehyde (4.24 mL, 30.3 mmol), piperidine (2.83 mL, 28.6 mmol) and 3 Å molecular sieves (8.75 g) in ethanol (125 mL) was refluxed for 5 hours. The resulting suspension was filtered and the filtrate was evaporated under reduced pressure. The residue was triturated with isopropyl ether and the precipitate collected by filtration and dried under vacuum to yield 6-[(E)-2-(2-ethoxyphenyl)vinyl]-3-methyl-5-nitro-1-propyl-1H-pyrimidine-2,4-dione (7.42 g, 75%) as a yellow solid.

b) To a stirred solution of the above compound (7.42 g, 20.6 mmol) in formic acid (185 mL) was slowly added sodium dithionite (21.1 g, 103 mmol) and the mixture was refluxed overnight. The resulting mixture was cooled to room temperature and water was added (500 mL). The precipitate was collected by filtration and washed with water, then dried under vacuum to yield 6-(2-ethoxyphenyl)-3-methyl-1-propyl-1,5-dihydropyrrolo[3,2-d]pyrimidine-2,4-dione (4.82 g, 72%) as a white solid.

δ(CDCl$_3$): 1.05 (t, 3H), 1.62 (t, 3H), 1.83 (m, 2H), 3.45 (s, 3H), 3.98 (t, 2H), 4.28 (q, 2H), 6.36 (s, 1H), 7.05 (m, 2H), 7.37 (t, 1H), 7.73 (d, 1H), 10.41 (bs, 1H).

Preparation 2

4-Ethoxy-3-(3-methyl-2,4-dioxo-1-propyl-2,3,4,5-tetrahydro-1H-pyrrolo[3,2-d]pyrimidin-6-yl)benzenesulphonyl chloride The title compound of Preparation 1 (2 g, 6.12 mmol) was added portionwise to a mixture of chlorosulphonic acid (10 mL) and thionyl chloride (1 mL) and stirred at 0° C. for 45 minutes. The reaction mixture was carefully poured into stirred ice-water and the aqueous suspension was partitioned between dichloromethane and brine, then the organic phase was separated, washed with water, dried (MgSO$_4$) and evaporated under reduced pressure to yield the title product (2.2 g, 87%) as a white solid.

δ(CDCl$_3$): 1.05 (t, 3H), 1.65 (t, 3H), 1.86 (m, 2H), 3.47 (s, 3H), 3.98 (t, 2H), 4.43 (q, 2H), 6.50 (s, 1H), 7.20 (d, 1H), 8.01 (d, 1H), 8.38 (s, 1H), 10.30 (bs, 1H).

Preparation 3

3-(7-Chloro-3-methyl-2,4-dioxo-1-propyl-2,3,4,5-tetrahydro-1H-pyrrolo[3,2-d]pyrimidin-6-yl)-4-ethoxybenzenesulphonyl chloride The title compound of Preparation 1 (5 g, 15.3 mmol) was added portionwise to a mixture of chlorosulphonic acid (25 mL) and sulphuryl chloride (12 mL) and stirred at 0° C. for 2 hours. The reaction mixture was carefully poured into stirred ice-water and the aqueous suspension was partitioned between dichloromethane and brine, then the organic phase was separated, washed with water, dried (MgSO$_4$) and evaporated under reduced pressure to yield the title compound (6.3 g, 90%) as a yellowish solid.

δ(CDCl$_3$): 1.05 (t, 3H), 1.48 (t, 3H), 1.83 (m, 2H), 3.31 (s, 3H), 4.30 (m, 4H), 7.19 (d, 1H), 8.09 (d, 1H), 8.40 (s, 1H), 10.92 (bs, 1H).

Preparation 4

3-(7-Bromo-3-methyl-2,4-dioxo-1-propyl-2,3,4,5-tetrahydro-1H-pyrrolo[3,2-d]pyrimidin-6-yl)-4-ethoxybenzenesulphonyl chloride To a solution of the title compound of Preparation 2 (0.7 g, 1.65 mmol) in glacial acetic acid (10 mL), was slowly added bromine (0.1 mL, 1.9 mmol) and the mixture was stirred at room temperature for 1 hour. The reaction mixture was then poured into ice-water and partitioned between dichloromethane and brine, the organic phase was separated, dried (MgSO$_4$) and evaporated under reduced pressure to yield the title product (0.67 g, 88%).

δ(CDCl$_3$): 1.05 (t, 3H), 1.48 (t, 3H), 1.83 (m, 2H), 3.32 (s, 3H), 4.26 (t, 2H), 4.35 (q, 2H), 7.19 (d, 1H), 8.16 (d, 1H), 8.39 (s, 1H), 10.61 (bs, 1H).

Preparation 5

3-Methyl-6-(2-propoxyphenyl)-1-propyl-1,5-dihydropyrrolo[3,2-d]pyrimidine-2,4-dione Obtained as a white solid (60% overall) from 3,6-dimethyl-5-nitro-1-propyl-1H-pyrimidine-2,4-dione and 2-propoxybenzaldehyde following the procedure described in Preparation 1.

δ(CDCl$_3$): 1.05 (t, 3H), 1.20 (t, 3H), 1.82 (m, 2H), 2.02 (m, 2H), 3.48 (s, 3H) 3.95 (t, 2H), 4.19 (t, 2H), 6.38 (s, 1H), 7.09 (m, 2H), 7.35 (t, 1H), 7.75 (d, 1H), 10.39 (bs, 1H).

Preparation 6

3-(3-methyl-2,4-dioxo-1-propyl-2,3,4,5-tetrahydro-1H-pyrrolo[3,2-d]pyrimidin-6-yl)-4-propoxybenzenesulphonyl chloride Obtained as a white solid (75%) from the title compound of Preparation 5, using the procedure described in Preparation 2.

δ(CDCl$_3$): 1.05 (t, 3H), 1.20 (t, 3H), 1.82 (m, 2H), 2.05 (m, 2H), 3.45 (s, 3H), 3.97 (t, 2H), 4.36 (t, 2H), 6.50 (s, 1H), 7.20 (d, 1H), 7.98 (d, 1H), 8.38 (s, 1H), 10.3 (bs, 1H).

Preparation 7

3-(7-Chloro-3-methyl-2,4-dioxo-1-propyl-2,3,4,5-tetrahydro-1H-pyrrolo[3,2-d]pyrimidin-6-yl)-4-propoxybenzenesulphonyl chloride Obtained as a yellowish solid (79%) from the title compound of Preparation 5, using the procedure described in Preparation 3.

δ(CDCl$_3$): 1.05 (m, 6H), 1.82 (m, 4H), 3.31 (s, 3H), 4.15 (t, 2H), 4.30 (t, 2H), 7.18 (d, 1H), 8.16 (d, 1H) 8.21 (s, 1H), 10.9 (bs, 1H).

Preparation 8

3-(7-Bromo-3-methyl-2,4-dioxo-1-propyl-2,3,4,5-tetrahydro-1H-pyrrolo[3,2-d]pyrimidin-6-yl)-4-propoxybenzenesulphonyl chloride Obtained as a white solid (83%) from the title compound of Preparation 6, using the procedure described in Preparation 4.

δ(CDCl$_3$): 1.05 (m, 6H), 1.82 (m, 4H), 3.30 (s, 3H), 4.16 (t, 2H), 4.35 (t, 2H), 7.18 (d, 1H), 8.16 (d, 1H), 8.36 (s, 1H), 11.3 (bs, 1H).

Preparation 9

6-(2-Ethoxyphenyl)-1-isobutyl-3-methyl-1,5-dihydropyrrolo[3,2-d]pyrimidine-2,4-dione Obtained as a white solid (40% overall) from 1-isobutil-3,6-dimethyl-1H-pyrimidine-2,4-dione and 2-ethoxybenzaldehyde following the procedure described in Preparation 1.

δ(CDCl$_3$): 1.02 (d, 6H), 1.61 (t, 3H), 2.25 (m, 1H), 3.44 (s, 3H), 3.80 (d, 2H), 4.26 (q, 2H), 6.36 (s, 1H), 7.02 (m, 2H), 7.38 (d, 1H), 7.75 (d, 1H), 10.38 (bs, 1H).

Preparation 10

3-(7-Chloro-1-isobutyl-3-methyl-2,4-dioxo-2,3,4,5-tetrahydro-1H-pyrrolo[3,2-d]pyrimidin-6-yl)-4-ethoxybenzenesulfonyl chloride Obtained as a yellowish solid (82%) from the title compound of Preparation 9, using the procedure described in Preparation 3.

δ(CDCl$_3$): 1.01 (d, 6H), 1.51 (t, 3H), 2.25 (m, 1H), 3.39 (s, 3H), 4.30 (m, 4H), 7.18 (d, 1H), 8.08 (dd, 1H), 8.50 (d, 1H), 10.30 (bs, 1H).

Preparation 11

4-Ethoxy-3-(7-iodo-3-methyl-2,4-dioxo-1-propyl-2,3,4,5-tetrahydro-1H-pyrrolo[3,2-d]pyrimidin-6-yl)benzenesulfonyl chloride Obtained as a yellow ochre solid (41%) from the title compound of Preparation 2 and iodine monochloride following the procedure described in Preparation 4.

δ(CDCl$_3$): 1.03 (t, 3H), 1.42 (t, 3H), 1.83 (m, 2H), 3.88 (s, 3H), 4.25 (m, 4H), 7.18 (d, 1H), 8.11 (dd, 1H), 8.19 (d, 1H), 11.38 (bs, 1H).

Preparation 12

3-acetyl-4-propoxybenzenesulfonyl chloride

To a mixture of chlorosulphonic acid (27 mL) and thionyl chloride (3.6 mL) at 0° C. was added portionwise 1-(2-propoxyphenyl)ethanone (5.0 g, 28.1 mmol). The resulting mixture was stirred at 0° C. for 20 min. and at room temperature overnight, poured cautiously into ice-water and extracted with methylene chloride. The organic solution was washed sequentially with water, aqueous sodium bicarbonate and brine, dried (MgSO$_4$), and the solvent removed under reduced pressure to yield the title compound (6.3 g, 81%) as an off-white solid.

Preparation 13

4-(3-Acetyl-4-propoxybenzenesulfonyl)piperazine-1-carboxylic acid ethyl ester

To a mixture of ethyl 1-piperazinecarboxylate (4.64 mL, 31.6 mmol) and triethylamine (3.8 mL, 27.2 mmol) in dichloromethane (80 mL) was added dropwise the title compound of Preparation 12 (6.26 g, 22.6 mmol) in dichloromethane (20 mL) and the resulting mixture was stirred at room temperature overnight. The reaction mixture was diluted with dichloromethane, washed with water, aqueous solution of sodium bicarbonate brine, dried (MgSO$_4$) and evaporated under reduced pressure. The resulting crude residue was purified by flash column chromatography on silica-gel (hexane-ethyl acetate 1:1) to yield the title compound (7.60 g, 84%) as a white solid.

δ(CDCl$_3$): 1.12 (t, 3H), 1.20 (t, 3H), 1.92 (m, 2H), 2.63 (s, 3H), 2.95 (m, 4H), 3.56 (m, 4H), 4.12 (m, 4H), 7.08 (d, 1H), 7.82 (d, 1H), 8.10 (s, 1H).

Preparation 14

4-[3-(2-Bromoethanoyl)-4-propoxybenzenesulfonyl]piperazine-1-carboxylic acid ethyl ester A solution of bromine (1.1 mL, 20.9 mmol) in chloroform (15 mL) was added dropwise to a solution of the title compound of Preparation 13 (7.60 g, 19.1 mmol) in chloroform (40 mL). After the addition of bromine is complete, a rapid stream of nitrogen is bubbled through the solution which is then stirred for 1 hour at room temperature under these conditions. The resulting mixture is diluted with chloroform and washed with aqueous sodium bicarbonate and brine, dried (MgSO$_4$) and evaporated under reduced pressure to yield the title compound (6.20 g, 67%) as a white solid.

δ(CDCl$_3$): 1.12 (t, 3H), 1.23 (t, 3H), 1.97 (m, 2H), 2.96 (m, 4H), 3.58 (m, 4H), 4.04 (q, 2H), 4.10 (q, 2H), 4.52 (s, 2H), 7.10 (d, 1H), 7.88 (d, 1H), 8.16 (s, 1H).

Preparation 15

1-[5-(Morpholine-4-sulfonyl)-2-propoxyphenyl]ethanone

Obtained as a white solid (quantitative yield) from the title compound of Preparation 12 and morpholine following the procedure of Preparation 13.

δ(CDCl$_3$): 1.14 (t, 3H), 1.92 (m, 2H), 2.64 (s, 3H), 2.98 (m, 4H), 3.72 (m, 4H), 4.14 (t, 2H), 7.10 (d, 1H), 7.84 (d, 1H), 8.11 (s, 1H).

Preparation 16

2-Bromo-1-[5-(morpholine-4-sulfonyl)-2-propoxyphenyl]ethanone

Obtained as a slightly orange solid (87%) from the title compound of Preparation 15 following the procedure of Preparation 14.

δ(CDCl$_3$): 1.07 (t, 3H), 1.98 (m, 2H), 2.92 (m, 4H), 3.76 (m, 4H), 4.12 (t, 2H), 4.52 (s, 2H), 7.12 (d, 1H), 7.88 (d, 1H), 8.18 (s, 1H).

EXAMPLES

TABLE 2

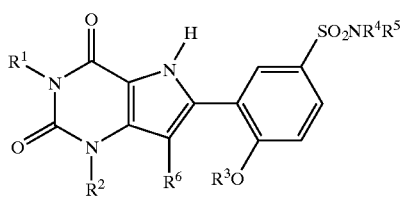

(II)

| Example No | R$^1$ | R$^2$ | R$^3$ | R$^6$ | NR$^4$R$^5$ |
|---|---|---|---|---|---|
| 1 | Me | nPr | Et | H | N-piperazinyl-N'-CH$_3$ |
| 2 | Me | nPr | Et | H | N-piperazinyl-NH |
| 3 | Me | nPr | Et | H | morpholinyl |
| 4 | Me | nPr | Et | H | NH-CH$_2$CH$_2$-N(CH$_3$)$_2$ |

TABLE 2-continued

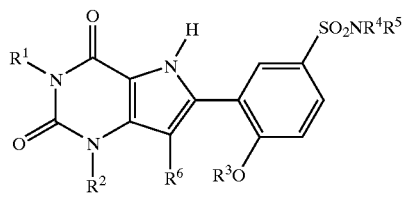

(II)

| Example No | R$^1$ | R$^2$ | R$^3$ | R$^6$ | NR$^4$R$^5$ |
|---|---|---|---|---|---|
| 5 | Me | nPr | Et | H | N-piperazinyl-N'-CH$_2$CH$_3$ |
| 6 | Me | nPr | Et | H | homopiperazinyl-N'-CH$_3$ |
| 7 | Me | nPr | Et | H | NH-CH$_2$CH$_2$-piperidinyl |
| 8 | Me | nPr | Et | H | NH-CH$_2$CH$_2$-morpholinyl |
| 9 | Me | nPr | Et | H | N-piperazinyl-N'-CH$_2$CH$_2$OH |
| 10 | Me | nPr | Et | H | NH-CH$_2$CH$_2$CH$_2$-morpholinyl |
| 11 | Me | nPr | Et | H | N-piperazinyl-N'-CH$_2$CH$_2$CH$_2$OH |
| 12 | Me | nPr | nPr | H | N-piperazinyl-N'-CH$_3$ |
| 13 | Me | nPr | nPr | H | N-piperazinyl-N'-CH$_2$CH$_3$ |
| 14 | Me | nPr | nPr | H | N-piperazinyl-N'-CH$_2$CH$_2$OH |
| 15 | Me | nPr | nPr | H | N-piperazinyl-NH |
| 16 | Me | nPr | nPr | H | morpholinyl |

TABLE 2-continued (II)

Structure: R¹-N and R²-N on pyrimidinedione fused to pyrrole bearing R⁶; aryl substituent with OR³ and SO₂NR⁴R⁵.

| Example No | R¹ | R² | R³ | R⁶ | NR⁴R⁵ |
|---|---|---|---|---|---|
| 17 | Me | nPr | nPr | H | -NH-CH₂CH₂-N(CH₃)₂ |
| 18 | Me | nPr | nPr | H | N(CH₂CH₂OH)₂ |
| 19 | Me | nPr | nPr | H | 4-methyl-1,4-diazepan-1-yl |
| 20 | Me | nPr | nPr | H | -NH-(4-methylpiperazin-1-yl) |
| 21 | Me | nPr | nPr | H | -NH-CH₂CH₂-(pyridin-2-yl) |
| 22 | Me | nPr | nPr | H | -NH-CH₂CH₂-(piperidin-1-yl) |
| 23 | Me | nPr | nPr | H | -NH-CH₂CH₂-(morpholin-4-yl) |
| 24 | Me | nPr | nPr | H | -NH-CH₂CH₂CH₂-(morpholin-4-yl) |
| 25 | Me | nPr | nPr | H | 4-(3-hydroxypropyl)piperazin-1-yl |
| 26 | Me | nPr | Et | Cl | piperazin-1-yl |
| 27 | Me | nPr | Et | Cl | 4-methylpiperazin-1-yl |
| 28 | Me | nPr | Et | Cl | 4-ethylpiperazin-1-yl |
| 29 | Me | nPr | Et | Cl | 4-(2-hydroxyethyl)piperazin-1-yl |
| 30 | Me | nPr | Et | Cl | -NH-CH₂CH₂-N(CH₃)₂ |
| 31 | Me | nPr | Et | Cl | 4-methyl-1,4-diazepan-1-yl |
| 32 | Me | nPr | Et | Cl | -NH-CH₂CH₂-(morpholin-4-yl) |
| 33 | Me | nPr | nPr | Cl | 4-methylpiperazin-1-yl |
| 34 | Me | nPr | nPr | Cl | 4-ethylpiperazin-1-yl |
| 35 | Me | nPr | nPr | Cl | 4-(2-hydroxyethyl)piperazin-1-yl |
| 36 | Me | nPr | Et | Br | morpholin-4-yl |
| 37 | Me | nPr | Et | Br | 4-methylpiperazin-1-yl |
| 38 | Me | nPr | Et | Br | 4-formylpiperazin-1-yl |
| 39 | Me | nPr | Et | Br | 4-ethylpiperazin-1-yl |
| 40 | Me | nPr | Et | Br | 4-methyl-1,4-diazepan-1-yl |

TABLE 2-continued (II)

| Example No | R¹ | R² | R³ | R⁶ | NR⁴R⁵ |
|---|---|---|---|---|---|
| 41 | Me | nPr | Et | Br | 4-amino-1-methylpiperazine (NH-piperazine-N-CH₃) |
| 42 | Me | nPr | Et | Br | NH-CH₂CH₂-(2-pyridyl) |
| 43 | Me | nPr | Et | Br | NH-CH₂CH₂-(1-piperidinyl) |
| 44 | Me | nPr | Et | Br | 4-(2-hydroxyethyl)piperazin-1-yl |
| 45 | Me | nPr | Et | Br | NH-CH₂CH₂-(4-morpholinyl) |
| 46 | Me | nPr | Et | Br | NH-CH₂CH₂CH₂-(4-morpholinyl) |
| 47 | Me | nPr | Et | Br | 4-(3-hydroxypropyl)piperazin-1-yl |
| 48 | Me | nPr | Et | Br | 4-(2-methoxyethyl)piperazin-1-yl |
| 49 | Me | nPr | nPr | Br | 4-morpholinyl |
| 50 | Me | nPr | nPr | Br | 4-methylpiperazin-1-yl |
| 51 | Me | nPr | nPr | Br | 4-formylpiperazin-1-yl |
| 52 | Me | nPr | nPr | Br | 4-ethylpiperazin-1-yl |
| 53 | Me | nPr | nPr | Br | 4-methyl-1,4-diazepan-1-yl |
| 54 | Me | nPr | nPr | Br | NH-CH₂CH₂-(4-morpholinyl) |
| 55 | Me | nPr | nPr | Br | 4-(2-hydroxyethyl)piperazin-1-yl |
| 56 | Me | nPr | nPr | Br | NH-CH₂CH₂CH₂-(4-morpholinyl) |
| 57 | Me | nPr | nPr | Br | 4-(3-hydroxypropyl)piperazin-1-yl |
| 58 | Me | iBu | Et | Cl | 4-methylpiperazin-1-yl |
| 59 | Me | iBu | Et | Cl | 4-ethylpiperazin-1-yl |
| 60 | Me | iBu | Et | Cl | 4-(2-hydroxyethyl)piperazin-1-yl |
| 61 | Me | iBu | Et | Cl | piperazin-1-yl |
| 62 | Me | nPr | Et | Cl | 4-methyl-4-oxido-piperazin-1-yl |
| 63 | Me | nPr | Et | Cl | NH-CH₂CH₂-NHMe |

TABLE 2-continued (II)

| Example No | R¹ | R² | R³ | R⁶ | NR⁴R⁵ |
|---|---|---|---|---|---|
| 64 | Me | nPr | Et | Cl | piperazine-N-(CH₂)₃-OH |
| 65 | Me | nPr | Et | Cl | -NH-CH₂CH₂-(2-pyridyl) |
| 66 | Me | nPr | Et | Cl | piperazine-N-CH₂CH₂-O-Et |
| 67 | Me | nPr | Et | Cl | piperazine-N-allyl |
| 68 | Me | nPr | Et | Cl | piperazine-N-iPr |
| 69 | Me | nPr | Et | Cl | octahydropyrrolo[1,2-a]pyrazine |
| 70 | Me | nPr | Et | Cl | octahydropyrrolo[1,2-a]pyrazine |
| 71 | Me | nPr | Et | Cl | octahydropyrrolo[1,2-a]pyrazine (Me-substituted) |
| 72 | Me | nPr | Et | Cl | octahydropyrrolo[1,2-a]pyrazine (OH-substituted) |
| 73 | Me | nPr | Et | Cl | N-methyl-diazabicyclic |
| 74 | Me | nPr | Et | I | N-methylpiperazine |
| 75 | Me | nPr | Et | I | 3-(dimethylamino)azetidine |
| 76 | Me | nPr | Et | I | N-methyl-homopiperazine |
| 77 | Me | nPr | Et | I | N-ethylpiperazine |
| 78 | Me | nPr | Et | I | N-allylpiperazine |
| 79 | Me | nPr | Et | I | N-isopropylpiperazine |
| 80 | Me | nPr | Et | I | piperazine-N-CH₂CH₂-OH |
| 81 | Me | nPr | Et | I | piperazine-N-CH₂CH₂-OCH₃ |
| 82 | Me | nPr | Et | I | piperazine-NH |
| 83 | Me | nPr | Et | I | 4-amino-2,2,6,6-tetramethylpiperidine |
| 84 | Me | nPr | Et | I | homopiperazine-N-CH₂CH₂-OH |

TABLE 2-continued (II)

| Example No | R¹ | R² | R³ | R⁶ | NR⁴R⁵ |
|---|---|---|---|---|---|
| 85 | Me | nPr | Et | I | (bicyclic diazabicyclo N-Me group) |

TABLE 3

(III)

| Example No | R¹ | R² | R³ | R⁶ | NR⁴R⁵ |
|---|---|---|---|---|---|
| 86 | Me | nPr | nPr | H | piperazine-N-CO₂Et |
| 87 | Me | nPr | nPr | H | piperazine-NH |
| 88 | Me | nPr | nPr | H | morpholine |
| 89 | Me | nPr | nPr | H | N-methylpiperazine (CH₃) |
| 90 | Me | nPr | nPr | (Me)₂NCH₂ | N-methylpiperazine (CH₃) |
| 91 | Me | nPr | nPr | H | N-propylpiperazine |
| 92 | Me | nPr | nPr | (Me)₂NCH₂ | piperazine-N-CO₂Et |
| 93 | Me | nPr | nPr | (Me)₂NCH₂ | morpholine |

TABLE 3-continued (III)

| Example No | R¹ | R² | R³ | R⁶ | NR⁴R⁵ |
|---|---|---|---|---|---|
| 94 | Me | nPr | nPr | MeOCH₂ | piperazine-N-CO₂Et |

Example 1

6-[2-Ethoxy-5-(4-methylpiperazine-1-sulphonyl) phenyl]-3-methyl-1-propyl-1,5-dihydropyrrolo[3,2-d]pyrimidine-2,4-dione To a mixture of the title compound of Preparation 2 (50 mg, 0.12 mmol) and polymer bound morpholine (85 mg, 2.75 mmol/g based on nitrogen analysis) in dichloromethane (3 mL) was added 1-methylpiperazine (0.015 mL, 0.13 mmol) and the resulting mixture was stirred at room temperature overnight. The reaction mixture was filtered and the filtrate was evaporated under reduced pressure. The residue was triturated with diethyl ether and the precipitate was collected by filtration and dried under vacuum to yield the title compound (22 mg, 39%) as a white solid.

ESI/MS m/e: 490 ([M+H]⁺, $C_{23}H_{31}N_5O_5S$). Retention Time (min.): 11.7.

Examples 2–11

The compounds of this invention were synthesized from the title compound of Preparation 2 following the procedure of example 1 and using the corresponding reactant respectively. The ESI/MS data, HtPLC retention times and yields are summarised in Table 4.

TABLE 4

| Example | Molecular Formula | ESI/MS m/e [M + H]⁺ | Retention Time (min.) | Yield % |
|---|---|---|---|---|
| 2 | $C_{22}H_{29}N_5O_5S$ | 476 | 11.7 | 72 |
| 3 | $C_{22}H_{28}N_4O_6S$ | 477 | 16.5 | 87 |
| 4 | $C_{22}H_{31}N_5O_5S$ | 478 | 11.0 | 70 |
| 5 | $C_{24}H_{33}N_5O_5S$ | 504 | 11.8 | 39 |
| 6 | $C_{24}H_{33}N_5O_5S$ | 504 | 11.5 | 73 |
| 7 | $C_{25}H_{35}N_5O_5S$ | 518 | 11.6 | 71 |
| 8 | $C_{24}H_{33}N_5O_6S$ | 520 | 11.3 | 48 |
| 9 | $C_{24}H_{33}N_5O_6S$ | 520 | 11.7 | 67 |
| 10 | $C_{25}H_{35}N_5O_6S$ | 534 | 11.2 | 57 |
| 11 | $C_{25}H_{35}N_5O_6S$ | 534 | 11.7 | 84 |

Example 12

3-Methyl-6-[5-(4-methylpiperazine-1-sulphonyl)-2-propoxyphenyl]-1-propyl-1,5-dihydropyrrolo[3,2-d]pyrimidine-2,4-dione To a mixture of the title compound of Preparation 6 (0.7 g, 1.6 mmol) and triethylamine (0.26 mL, 1.9 mmol) in dichloromethane (30 mL) was added dropwise 1-methylpiperazine (0.21 mL, 1.9 mmol) and the resulting mixture was stirred at room temperature overnight. The reaction mixture was diluted with dichloromethane, washed with aqueous solution of sodium bicarbonate in water, dried (MgSO$_4$) and evaporated under reduced pressure. The resulting crude residue was purified by flash column chromatography on silica-gel (dichloromethane-methanol 9:1)to yield the title compound (240 mg, 30%).

m.p.: 198° C.

δ(DMSO-d6): 0.93 (t, 3H), 1.06 (t, 3H), 1.70 (m, 2H), 1.88 (m, 2H), 2.14 (s, 3H), 2.37 (m, 4H), 2.93 (m, 4H), 3.28 (s, 3H), 3.87 (t, 2H), 4.18 (t, 2H), 6.77 (s, 1H), 7.36 (d, 1H), 7.67 (dd, 1H), 8.19 (d, 1H), 12.54 (bs, 1H).

Example 13

6-[5-(4-Ethylpiperazine-1-sulphonyl)-2-propoxyphenyl]-3-methyl-1-propyl-1,5-dihydropyrrolo[3,2-d]pyrimidine-2,4-dione Obtained as a white solid (32%) from the title compound of Preparation 6 and 1-ethylpiperazine following the procedure of example 12.

m.p.: 194° C.

δ(DMSO-d6): 0.92 (m, 6H), 1.06 (t, 3H), 1.69 (m, 2H), 1.85 (m, 2H), 2.29 (q, 2H), 2.42 (m, 4H), 2.91 (m, 4H), 3.28 (s, 3H), 3.87 (t, 2H), 4.18 (t, 2H), 6.77 (s, 1H), 7.36 (d, 1H), 7.67 (dd, 1H), 8.19 (d, 1H), 12.55 (bs, 1H).

Elemental analysis calculated for $C_{25}H_{35}N_5O_5S$: C, 58.01; H, 6.82; N, 13.53; S, 6.19. Found: C, 57.13; H, 6.87; N, 12.97; S, 6.08.

Example 14

6-{5-[4-(2-Hydroxyethyl)piperazine-1-sulphonyl]-2-propoxyphenyl}-3-methyl-1-propyl-1,5-dihydropyrrolo[3,2-d]pyrimidine-2,4-dione Obtained as a white solid (35%) from the title compound of Preparation 6 and 1-(2-hydroxyethyl)piperazine following the procedure of example 12.

m.p.: 237° C.

δ(DMSO-d6): 0.93 (t, 3H), 1.06 (t, 3H), 1.70 (m, 2H), 1.88 (m, 2H), 2.36 (t, 2H), 2.50 (m, 4H), 2.91 (m, 4H), 3.28 (s, 3H), 3.41 (q, 2H), 3.86 (t, 2H), 4.18 (t, 2H), 4.37 (t, 1H), 6.77 (s, 1H), 7.36 (d, 1H), 7.67 (dd, 1H), 8.20 (d, 1H), 12.55 (bs, 1H).

Example 15

3-Methyl-6-[5-(piperazine-1-sulfonyl)-2-propoxyphenyl]-1- propyl-1,5-dihydropyrrolo[3,2-d] pyrimidine-2,4-dione Obtained as a white solid (40%) from the title compound of Preparation 6 and piperazine following the procedure of example 12.

m.p.: 240° C.

δ(DMSO-d6): 0.94 (t, 3H), 1.07 (t, 3H), 1.70 (q, 2H), 1.88 (q, 2H), 2.74 (m, 4H), 2.82 (m, 4H), 3.36 (s, 3H), 3.88 (t, 2H), 4.18 (t, 2H), 6.78 (s, 1H), 7.36 (d, 1H), 7.66 (dd, 1H), 8.19 (d, 1H), 12.56 (bs, 1H).

Elemental analysis calculated for $C_{23}H_{31}N_5O_5S$: C, 56.43; H, 6.38; N, 14.31; S, 6.55. Found: C, 56.18; H, 6.50; N, 13.86; S, 6.60.

Examples 16–25

These compounds were synthesized from the title compound of Preparation 6 following the procedure of example 1 and using the corresponding reactant respectively. The ESI/MS data, HPLC retention times and yields are summarised in Table 5.

TABLE 5

| Example | Molecular Formula | ESI/MS m/e [M + H]$^+$ | Retention Time (min.) | Yield % |
|---|---|---|---|---|
| 16 | $C_{23}H_{30}N_4O_6S$ | 491 | 17.5 | 58 |
| 17 | $C_{23}H_{33}N_5O_5S$ | 492 | 11.8 | 51 |
| 18 | $C_{23}H_{32}N_4O_7S$ | 509 | 15.7 | 67 |
| 19 | $C_{25}H_{35}N_5O_5S$ | 518 | 12.3 | 67 |
| 20 | $C_{24}H_{34}N_6O_5S$ | 519 | 12.1 | 57 |
| 21 | $C_{26}H_{31}N_5O_5S$ | 526 | 15.0 | 29 |
| 22 | $C_{26}H_{37}N_5O_5S$ | 532 | 12.3 | 60 |
| 23 | $C_{25}H_{35}N_5O_6S$ | 534 | 12.1 | 40 |
| 24 | $C_{26}H_{37}N_5O_6S$ | 548 | 12.0 | 40 |
| 25 | $C_{26}H_{37}N_5O_6S$ | 548 | 12.4 | 60 |

Example 26

7-Chloro-6-[2-ethoxy-5-(piperazine-1-sulfonyl) phenyl]-3-methyl-1-propyl-1,5-dihydropyrrolo[3,2-d]pyrimidine-2,4-dione Obtained as a white solid (32%) from the title compound of Preparation 3 and piperazine following the procedure of example 12.

m.p.: 257° C.

δ(DMSO-d6): 0.94 (t, 3H), 1.32 (t, 3H), 1.70 (m, 2H), 2.73 (m, 4H), 2.81 (m, 4H), 3.27 (s, 3H), 3.34 (bs, 1H), 4.18 (m, 4H), 7.38 (d, 1H), 7.63 (d, 1H), 7.78 (dd, 1H), 12.86 (bs, 1H).

Elemental analysis calculated for $C_{22}H_{28}ClN_5O_5S$: C, 51.81; H, 5.53; N, 13.73; S, 6.29. Found: C, 51.26; H, 5.50; N, 13.39; S, 6.22.

Example 27

7-Chloro-6-[2-ethoxy-5-(4-methylpiperazine-1-sulfonyl)phenyl]-3-methyl-1-propyl-1,5-dihydropyrrolo[3,2-d]pyrimidine-2,4-dione Obtained as a white solid (50%) from the title compound of Preparation 3 and 1-methylpiperazine following the procedure of example 12.

m.p.: 256° C.

δ(DMSO-d6): 0.94 (t, 3H), 1.32 (t, 3H), 1.70 (m, 2H), 2.15 (s, 3H), 2.38 (m, 4H), 2.91 (m, 4H), 3.28 (s, 3H), 4.17 (m, 4H), 7.38 (d, 1H), 7.63 (d, 1H), 7.80 (dd, 1H), 12.87 (bs, 1H).

Elemental analysis calculated for $C_{23}H_{30}ClN_5O_5S$: C, 52.72; H, 5.77; N, 13.37; S, 6.12. Found: C, 52.33; H, 5.93; N, 12.97; S, 6.25.

Example 28

7-Chloro-6-[2-ethoxy-5-(4-ethylpiperazine-1-sulfonyl)phenyl]-3-methyl-1-propyl-1,5-dihydropyrrolo[3,2-d]pyrimidine-2,4-dione Obtained as a white solid (36%) from the title compound of Preparation 3 and 1-ethylpiperazine following the procedure of example 12.

m.p.: 213° C.

δ(DMSO-d6): 0.94 (t, 3H), 1.32 (t, 3H), 1.70 (m, 2H), 2.31 (q, 2H), 2.43 (m, 4H), 2.92 (m, 4H), 3.28 (s, 3H), 4.19 (m, 4H), 7.39 (d, 1H), 7.63 (d, 1H), 7.80 (dd, 1H), 12.86 (bs, 1H).

Example 29

7-Chloro-6-{2-ethoxy-5-[4-(2-hydroxyethyl)piperazine-1-sulfonyl]phenyl}-3-methyl-1-propyl-1,5-dihydropyrrolo[3,2-d]pyrimidine-2,4-dione Obtained as a white solid (30%) from the title compound of Preparation 3 and 1-(2-hydroxyethyl)piperazine following the procedure of example 12.

m.p.: 146° C.

δ(DMSO-d6): 0.94 (t, 3H), 1.32 (t, 3H), 1.70 (m, 2H), 2.38 (m, 2H), 2.50 (m, 4H), 2.90 (m, 4H), 3.28 (s, 3H), 3.43 (m, 2H), 4.18 (m, 4H), 4.41 (bs, 1H), 7.39 (d, 1H), 7.63 (d, 1H), 7.79 (dd, 1H), 12.87 (bs, 1H).

Examples 30, 31 and 32

Obtained from the title compound of Preparation 3 following the procedure of example 1 and using the corresponding reactant respectively. The ESI/MS data, HPLC retention times and yields are summarised in Table 6.

TABLE 6

| Example | Molecular Formula | ESI/MS m/e [M + H]⁺ | Retention Time | Yield % |
|---|---|---|---|---|
| 30 | $C_{22}H_{30}ClN_5O_5S$ | 512 | 11.9 | 61 |
| 31 | $C_{24}H_{32}ClN_5O_5S$ | 538 | 12.3 | 68 |
| 32 | $C_{24}H_{32}ClN_5O_6S$ | 554 | 12.2 | 62 |

Example 33

7-Chloro-3-methyl-6-[5-(4-methylpiperazine-1-sulfonyl)-2-propoxyphenyl]-1-propyl-1,5-dihydropyrrolo[3,2-d]pyrimidine-2,4-dione Obtained as a white solid (45%) from the title compound of Preparation 7 and 1-methylpiperazine following the procedure of example 12.

m.p.: 197° C.

δ(DMSO-d6): 0.93 (m, 6H), 1.72 (m, 4H), 2.15 (s, 3H), 2.38 (m, 4H), 2.91 (m, 4H), 3.27 (s, 3H), 4.09 (t, 2H), 4.15 (t, 2H), 7.39 (d, 1H), 7.62 (d, 1H), 7.80 (dd, 1H), 12.84 (bs, 1H).

Example 34

7-Chloro-6-[5-(4-ethylpiperazine-1-sulfonyl)-2-propoxyphenyl]-3-methyl-1-propyl-1,5-dihydropyrrolo[3,2-d]pyrimidine-2,4-dione Obtained as a white solid (42%) from the title compound of Preparation 7 and 1-ethylpiperazine following the procedure of example 12.

m.p.: 215° C.

δ(DMSO-d6): 0.92 (m, 9H), 1.67 (m, 4H), 2.40 (m, 6H), 2.89 (m, 4H), 3.25 (s, 3H), 4.09 (m, 4H), 7.38 (d, 1H), 7.62 (d, 1H), 7.78 (dd, 1H), 12.83 (bs, 1H).

Example 35

7-Chloro-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione Obtained as a white solid (60%) from the title compound of Preparation 7 and 1-(2-hydroxyethyl)piperazine following the procedure of example 12.

m.p.: 140° C.

δ(DMSO-d6): 0.91 (m, 6H), 1.67 (m, 4H), 2.34 (t, 2H), 2.47 (m, 4H), 2.87 (m, 4H), 3.25 (s, 3H), 3.39 (q, 2H), 4.10 (m, 4H), 4.37 (t, 1H), 7.37 (d, 1H), 7.60 (d, 1H), 7.77 (dd, 1H), 12.81 (bs, 1H).

Examples 36–48

The compounds of this invention were synthesized from the title compound of Preparation 4 following the procedure of example 1 and using the corresponding reactants respectively. The ESI/MS data, HPLC retention times and yields are sunnmarised in Table 7.

TABLE 7

| Example | Molecular Formula | ESI/MS m/e [M + H]⁺ | Retention Time | Yield % |
|---|---|---|---|---|
| 36 | $C_{22}H_{27}BrN_4O_6S$ | 555 | 17.4 | 84 |
| 37 | $C_{23}H_{30}BrN_5O_5S$ | 568 | 12.0 | 84 |
| 38 | $C_{23}H_{28}BrN_5O_6S$ | 582 | 16.2 | 84 |
| 39 | $C_{24}H_{32}BrN_5O_5S$ | 582 | 12.2 | 50 |
| 40 | $C_{24}H_{32}BrN_5O_5S$ | 582 | 12.0 | 85 |
| 41 | $C_{23}H_{31}BrN_6O_5S$ | 583 | 11.6 | 78 |
| 42 | $C_{25}H_{28}BrN_5O_5S$ | 590 | 14.8 | 81 |
| 43 | $C_{25}H_{34}BrN_5O_5S$ | 596 | 12.1 | 59 |
| 44 | $C_{24}H_{32}BrN_5O_6S$ | 598 | 12.1 | 57 |
| 45 | $C_{24}H_{32}BrN_5O_6S$ | 598 | 11.9 | 80 |
| 46 | $C_{25}H_{34}BrN_5O_6S$ | 612 | 11.7 | 45 |
| 47 | $C_{25}H_{34}BrN_5O_6S$ | 612 | 12.1 | 78 |
| 48 | $C_{25}H_{34}BrN_5O_6S$ | 612 | 12.5 | 80 |

Examples 49–57

The compounds of this invention were synthesized from the title compound of Preparation 8 following the procedure of example 1 and using the corresponding reactants respectively. The ESI/MS data, HPLC retention times and yields are summarised in Table 8.

TABLE 8

| Example | Molecular Formula | ESI/MS m/e [M + H]⁺ | Retention Time | Yield % |
|---|---|---|---|---|
| 49 | $C_{23}H_{29}BrN_4O_6S$ | 569 | 18.2 | 80 |
| 50 | $C_{24}H_{32}BrN_5O_5S$ | 582 | 12.9 | 87 |
| 51 | $C_{24}H_{30}BrN_5O_6S$ | 596 | 17.0 | 96 |
| 52 | $C_{25}H_{34}BrN_5O_5S$ | 596 | 12.9 | 74 |
| 53 | $C_{25}H_{34}BrN_5O_5S$ | 596 | 12.8 | 78 |
| 54 | $C_{25}H_{34}BrN_5O_6S$ | 612 | 12.7 | 81 |
| 55 | $C_{25}H_{34}BrN_5O_6S$ | 612 | 12.9 | 57 |
| 56 | $C_{26}H_{36}BrN_5O_6S$ | 626 | 12.5 | 68 |
| 57 | $C_{26}H_{36}BrN_5O_6S$ | 626 | 12.8 | 75 |

Example 58

7-Chloro-6-[2-ethoxy-5-(4-methylpiperazine-1-sulfonyl)phenyl]-1-isobutyl-3-methyl-1,5-dihydropyrrolo[3,2-d]pyrimidine-2,4-dione Obtained as a white solid (51%) from the title compound of Preparation 10 and 1-methylpiperazine following the procedure of example 12.

m.p.: 257° C.

δ(DMSO-d6): 0.92 (d, 6H), 1.31 (t, 3H), 2.13 (m, 1H), 2.15 (t, 3H), 2.38 (m, 4H), 2.92 (m, 4H), 3.28 (s, 3H), 4.05 (d, 2H), 4.19 (q, 2H), 7.37 (d, 1H), 7.63 (s, 1H), 7.80 (d, 1H), 12.89 (bs, 1H).

Example 59

7-Chloro-6-[2-ethoxy-5-(4-ethylpiperazine-1-sulfonyl)phenyl]-1-isobutyl-3-methyl-1,5-dihydropyrrolo[3,2-d]pyrimidine-2,4-dione Obtained as a white solid (48%) from the title compound of Preparation 10 and 1-ethylpiperazine following the procedure of example 12.

m.p.: 239° C.

δ(DMSO-d6): 0.93 (d, 6H), 1.31 (t, 3H), 2.13 (m, 1H), 2.33 (m, 2H), 2.44 (m, 4H), 2.92 (m, 4H), 3.28 (s, 3H), 4.06 (d, 2H), 4.19 (q, 2H), 7.37 (d, 1H), 7.63 (s, 1H), 7.81 (d, 1H), 12.89 (bs, 1H).

Example 60

7-Chloro-6-{2-ethoxy-5-[4-(2-hydroxyethyl)piperazine-1-sulfonyl]phenyl}-1-isobutyl-3-methyl-1,5-dihydropyrrolo[3,2-d]pyrimidine-2,4-dione Obtained as a white solid (40%) from the title compound of Preparation 10 and 1-(2-hydroxiethyl)piperazine following the procedure of example 12.

m.p.: 148° C.

δ(DMSO-d6): 0.92 (d, 6H), 1.31 (t, 3H), 2.14 (m, 1H), 2.37 (t, 2H), 2.50 (m, 4H), 2.91 (m, 4H), 3.28 (s, 3H), 3.43 (m, 2H), 4.06 (d, 2H), 4.19 (q, 2H), 4.39 (bs, 1H), 7.38 (d, 1H), 7.63 (s, 1H), 7.81 (d, 1H), 12.87 (bs, 1H).

Example 61

7-Chloro-6-[2-ethoxy-5-(piperazine-1-sulfonyl)phenyl]-1-isobutyl-3-methyl-1,5-dihydropyrrolo[3,2-d]pyrimidine-2,4-dione Obtained as a white solid (28%) from the title compound of Preparation 10 and piperazine following the procedure of example 12.

m.p.: 246° C.

δ(DMSO-d6): 0.93 (d, 6H), 1.31 (t, 3H), 2.12 (m, 1H), 2.76 (m, 4H), 2.82 (m, 4H), 3.28 (s, 3H), 4.06 (d, 2H), 4.18 (q, 2H), 7.38 (d, 1H), 7.64 (s, 1H), 7.80 (d, 1H).

Example 62

7-Chloro-6-[2-ethoxy-5-(4-methyl-4-oxypiperazine-1-sulfonyl)phenyl]-3-methyl-1-propyl-1,5-dihydropyrrolo[3,2-d]pyrimidine-2,4-dione To a solution of the title compound of example 27 (300 mg, 0.57 mmol) in dichloromethane (20 mL) at 0° C., was slowly added 3-chloroperoxybenzoic acid (136 mg, 0.63 mmol). The mixture was stirred at room temperature for 2 hours and then poured into an aqueous solution of sodium bicarbonate. The precipitate was collected by filtration, washed with water and dried to yield the title product (300 mg, 97%) as a white solid.

m.p.: 227° C.

δ(DMSO-d6): 0.93 (t, 3H), 1.32 (t, 3H), 1.69 (m, 2H), 2.9–3.5 (m, 8H), 3.26 (s, 3H), 4.20 (m 4H), 7.38 (d, 1H), 7.69 (s, 1H), 7.80 (d, 1H).

Example 63

3-(7-Chloro-3-methyl-2,4-dioxo-1-propyl-2,3,4,5-tetrahydro-1H-pyrrolo[3,2-d]pyrimidin-6-yl)-4-ethoxy-N-(2-methylaminoethyl)benzenesulfonamide a) Following the procedure of example 12, from the title compound of Preparation 3 (1.64 g, 3.56 mmol) and N-benzyl-N-methylethylenediamine (0.67 g, 4.1 mmol), N-[2-(benzyl-methyl-amino)ethyl]-3-(7-chloro-3-methyl-2,4-dioxo-1-propyl-2,3,4,5-tetrahydro-1H-pyrrolo[3,2-d]pyrimidin-6-yl)-4-ethoxy-benzenesulfonamide (0.93 g, 44%) was obtained.

b) A mixture of the above compound (0.5 g, 0.85 mmol), ethanol (40 mL), concentrated hydrochloric acid (0.1 mL) and palladium hydroxide (80 mg) was hydrogenated for 4 hours at 30 p.s.i. The catalyst was removed by filtration through celite and the filtrate was evaporated under reduced pressure. The resulting crude product was purified by flash column chromatography on silica gel (dichloromethane-ethanol-ammonium hydroxyde 100:8:1) to yield the title compound (0.18 g, 43%) as an off-white solid.

m.p.: 226° C.

δ(DMSO-d6): 0.94 (t, 3H), 1.29 (t, 3H), 1.70 (m, 2H), 2.18 (s, 3H), 2.49 (t, 2H), 2.81 (t, 2H), 3.27 (s, 3H), 4.20 (m, 4H), 7.33 (d, 1H), 7.74 (s, 1H), 7.86 (d, 1H).

Examples 64–73

The compounds of this invention were synthesized from the title compound of Preparation 3 following the procedure of example 1 and using the corresponding reactants respectively. The ESI/MS data, HPLC retention times and yields are summansed in Table 9.

TABLE 9

| Example | Molecular Formula | ESI/MS m/e [M + H]+ | Retention Time (min.) | Yield % |
|---|---|---|---|---|
| 64 | $C_{25}H_{34}ClN_5O_6S$ | 568 | 12.4 | 62 |
| 65 | $C_{25}H_{28}ClN_5O_5S$ | 546 | 15.1 | 60 |
| 66 | $C_{26}H_{36}ClN_5O_6S$ | 582 | 13.3 | 55 |
| 67 | $C_{25}H_{32}ClN_5O_5S$ | 550 | 13.2 | 68 |
| 68 | $C_{25}H_{34}ClN_5O_5S$ | 552 | 12.6 | 58 |
| 69 | $C_{25}H_{32}ClN_5O_5S$ | 550 | 8.5 | 72 |
| 70 | $C_{25}H_{32}ClN_5O_5S$ | 550 | 8.5 | 71 |
| 71 | $C_{26}H_{34}ClN_5O_5S$ | 564 | 8.4 | 56 |
| 72 | $C_{25}H_{32}ClN_5O_6S$ | 566 | 8.5 | 25 |
| 73 | $C_{24}H_{30}ClN_5O_5S$ | 536 | 8.1 | 66 |

Examples 74–85

The compounds of this invention were synthesized from the title compound of Preparation 11 following the procedure of example 1 and using the corresponding reactants respectively. The ESI/MS data, HPLC retention times and yields are summarised in Table 10.

TABLE 10

| Example | Molecular Formula | ESI/MS m/e [M + H]+ | Retention Time (min.) | Yield % |
|---|---|---|---|---|
| 74 | $C_{23}H_{30}IN_5O_5S$ | 616 | 8.2 | 55 |
| 75 | $C_{23}H_{30}IN_5O_5S$ | 616 | 8.3 | 45 |
| 76 | $C_{24}H_{32}IN_5O_5S$ | 630 | 8.2 | 62 |
| 77 | $C_{24}H_{32}IN_5O_5S$ | 630 | 8.3 | 65 |
| 78 | $C_{25}H_{32}IN_5O_5S$ | 642 | 8.8 | 72 |
| 79 | $C_{25}H_{34}IN_5O_5S$ | 644 | 8.3 | 75 |
| 80 | $C_{24}H_{32}IN_5O_6S$ | 646 | 8.2 | 55 |
| 81 | $C_{25}H_{34}IN_5O_6S$ | 660 | 8.5 | 42 |
| 82 | $C_{22}H_{28}IN_5O_5S$ | 602 | 8.2 | 22 |
| 83 | $C_{27}H_{38}IN_5O_5S$ | 672 | 8.2 | 35 |
| 84 | $C_{25}H_{34}IN_5O_6S$ | 660 | 8.2 | 44 |
| 85 | $C_{24}H_{30}IN_5O_5S$ | 628 | 8.1 | 65 |

Example 86

4-[3-(3-Methyl-2,4-dioxo-1-propyl-2,3,4,7-tetrahydro-1H-pyrrolo[2,3-d]pyrimidin-6-yl)-4-propoxybenzenesulfonyl]piperazine-1-carboxylic acid ethyl ester A mixture of 6-amino-3-methyl-1-propyl-1H-pyrimidine-2,4-dione (2.0 g, 10.8 mmol) and the title compound of Preparation 14 (6.2 g, 13.0 mmol) in N,N-dimethylformamide (55 mL) was refluxed for 18 h. The resulting solution was evaporated under reduced pressure and the resulting residue was partitioned between ethyl acetate and aqueous sodium bicarbonate solution, then the organic phase separated, washed with water and brine, dried (MgSO$_4$) and evaporated under reduced pressure. The resulting crude residue was purified by flash column chromatography on silica-gel (hexane-ethyl acetate 1:1→1:3) to yield the title compound (2.80 g, 46%) as a white solid.

m.p.: 181° C.

δ(DMSO-d6): 0.93 (t, 3H), 1.04 (t, 3H), 1.12 (t, 3H), 1.71 (m, 2H), 1.83 (m, 2H), 2.89 (m, 4H), 3.24 (s, 3H), 3.45 (m, 4H), 3.97 (q, 2H), 4.04 (t, 2H), 4.14 (t, 2H), 6.90 (s, 1H), 7.32 (d, 1H), 7.62 (d, 1H), 7.88 (s, 1H), 11.62 (s, 1H).

Example 87

3-Methyl-6-[5-(piperazine-1-sulfonyl)-2-propoxyphenyl]-1-propyl-1,7-dihydropyrrolo[2,3-d]pyrimidine-2,4-dione A mixture of the title compound of Example 86 (0.5 g, 0.89 mmol) and potassium hydroxide (0.58 g, 8.90 mmol, 85%) in isopropanol (20 mL) was refluxed for 18 h. The resulting mixture was evaporated under reduced pressure and the resulting residue was acidified with 6N hydrochloric acid. Then it was basified with aqueous sodium bicarbonate solution and extracted with dichloromethane. The organic extracts were dried (MgSO$_4$) and evaporated under reduced pressure. The resulting crude residue was purified by flash column chromatography on silica-gel (dichloromethane-ethanol-ammonium hydroxide 180:8:1) to yield the title compound (0.24 g, 55%) as a white solid.

m.p.: 237° C.

δ(DMSO-d6): 0.95 (t, 3H), 1.04 (t, 3H), 1.69 (m, 2H), 1.82 (m, 2H), 2.71 (m, 4H), 2.77 (m, 4H), 3.24 (s, 3H), 4.04 (t, 2H), 4.14 (t, 2H), 6.89 (s, 1H), 7.33 (d, 1H), 7.60 (d, 1H), 7.90 (s, 1H).

Example 88

3-Methyl-6-[5-(morpholine-4-sulfonyl)-2-propoxyphenyl]-1-propyl-1,7-dihydropyrrolo[2,3-d]pyrimidine-2,4-dione Obtained as a white solid (28%) from the title compound of Preparation 16 and 6-amino-3-methyl-1-propyl-1H-pyrimidine-2,4-dione following the procedure of Example 86.

m.p.: 271° C.

δ(DMSO-d6): 0.96 (t, 3H), 1.02 (t, 3H), 1.67 (m, 2H), 1.84 (m, 2H), 2.82 (m, 4H), 3.22 (s, 3H), 3.63 (m, 4H), 4.03 (t, 2H), 4.17 (t, 2H), 6.89 (s, 1H), 7.36 (d, 1H), 7.62 (d, 1H), 7.89 (s, 1H), 11.63 (s, 1H).

Example 89

3-Methyl-6-[5-(4-methylpiperazine-1-sulfonyl)-2-propoxyphenyl]-1-propyl-1,7-dihydropyrrolo[2,3-d]pyrimidine-2,4-dione A mixture of the title compound of Example 87 (0.4 g, 0.82 mmol), formaldehyde (0.14 mL, 37% in water, 1.63 mmol) and palladium 10% on activated carbon (40 mg) was hydrogenated for 2 h. The catalyst was removed by filtration through celite and the filtrate was evaporated under reduced pressure. The resulting crude product was purified by flash column chromatography on silica-gel (dichloromethane-ethanol-ammonium hydroxide 180:8:1) to yield the title compound (0.07 g, 17%) as an off-white solid.

m.p.: 240° C.

δ(DMSO-d6): 0.93 (t, 3H), 1.05 (t, 3H9, 1.73 (m, 2H), 1.86 (m, 2H), 2.13 (s, 3H), 2.36 (m, 4H), 2.89 (m, 4H), 3.23 (s, 3H), 4.03 (t, 2H), 4.14 (t, 2H), 6.87 (s, 1H), 7.33 (d, 1H), 7.63 (d, 1H), 7.88 (s, 1H), 11.63 (bs, 1H).

Example 90

5-Dimethylaminomethyl-3-methyl-6-[5-(4-methylpiperazine-1-sulfonyl)-2-propoxyphenyl]-1-propyl-1,7-dihydropyrrolo[2,3-d]pyrimidine-2,4-dione A mixture of the title compound of Example 89 (30 mg, 0.06 mmol) and N,N-dimethylmethyleneiminium iodide (57 mg, 0.23 mmol) in anhydrous dichloromethane was stirred at room temperature overnight. The reaction mixture was purified by solid phase extraction using a Varian Bond Elut SCX cartridge (methanol for washing, methanol-ammonia for elution) to yield the title compound (32 mg, 95%).

ESI/MS m/e: 461 ([M+H]$^+$, C$_{27}$H$_{40}$N$_6$O$_5$S).

Retention Time (min.): 7.6.

Example 91

3-Methyl-6-[2-propoxy-5-(4-propyl-piperazine-1-sulfonyl)phenyl]-1-propyl-1,7-dihydropyrrolo[2,3-d]pyrimidine-2,4-dione A mixture of the title compound of example 87 (50 mg, 0.1 mmol), propanal (0.073 mL, 1 mmol) and 3 Å molecular sieves (300 mg) in methanol (2 mL) and acetic acid (0.1 mL), was stirred at room temperature for 4 hours. Then sodium cianoborohydride (32 mg, 0.51 mmol) was slowly added and the mixture was stirred at room temperature overnight. The reaction mixture was purified by solid phase extraction using a Varian Bond Elut SCX cartridge (methanol for washing, methanol-ammonia for elution) to yield the title compound (40 mg, 72%).

ESI/MS m/e: 532 ([M+H]$^+$, C$_{26}$H$_{37}$N$_5$O$_5$S).

Retention Time (min.): 11.9.

Example 92

4-[3-(5-Dimethylaminomethyl-3-methyl-2,4-dioxo-1-propyl-2,3,4,7-tetrahydro-1H-pyrrolo[2,3-d]pyrimidin-6-yl)-4-propoxybenzenesulfonyl]-piperazine-1-carboxylic acid ethyl ester Obtained as a white solid (89%) from the title compound of example 86 following the procedure of example 90.

ESI/MS m/e: 619 ([M+H]$^+$, C$_{29}$H$_{42}$N$_6$O$_7$S).

Retention Time (min.): 11.6.

Example 93

5-Dimethylaminomethyl-3-methyl-6-[5-(morpholine-4-sulfonyl)-2-propoxyphenyl]-1-propyl-1,7-dihydropyrrolo[2,3-d]pyrimidine-2,4-dione Obtained as a white solid (92%) from the title compound of example 88 following the procedure of example 90.

ESI/MS m/e: 548 ([M+H]$^+$, $C_{26}H_{37}N_5O_6S$).
Retention Time (min.): 10.4.

Example 94

4-[3-(5-Methoxymethyl-3-methyl-2,4-dioxo-1-propyl-2,3,4,7-tetrahydro-1H-pyrrolo[2,3-d]pyrimidin-6-yl)-4-propoxybenzenesulfonyl]piperazine-1-carboxylic acid ethyl ester To a solution of the title compound of example 92 (50 mg, 0.08 mmol) in methanol (5 mL) was added methyl iodide (0.015 mL, 0.24 mmol) and the mixture was stirred for 3 hours at room temperature. Then sodium methoxide (0.03 mL from a solution 5.3M in methanol, 0.16 mmol) was added and the mixture was stirred at room temperature overnight. The solvent was removed under reduced pressure and the residue partitioned between water and dichloromethane. The organic phase was washed with brine, dried (MgSO$_4$) and evaporated to yield the title compound,(34 mg, 71%) as a white solid.

ESI/MS m/e: 606 ([M+H]$^+$, $C_{28}H_{39}N_5O_8S$).
Retention Time (min.): 11.0.

The following examples illustrate pharmaceutical compositions according to the present invention and procedure for their preparation.

Compositon Example 1

50,000 capsules each containing 100 mg of 3-methyl-6-[5-(4-methylpiperazine-1-sulphonyl)-2-propoxyphenyl]-1-propyl-1,5-dihydropyrrolo[3,2-d]pyrimidine-2,4-dione (active ingredient) were prepared according to the following formulation:

| | |
|---|---|
| Active ingredient | 5 Kg |
| Lactose monohydrate | 10 Kg |
| Colloidal silicone dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets each containing 50 mg of 6-[5-(4-ethylpiperazine-1-sulphonyl)-2-propoxyphenyl]-3-methyl-1-propyl-1,5-dihydropyrrolo[3,2-d]pyrimidine-2,4-dione (active ingredient) were prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

What is claimed is:
1. A 6-phenylpyrrolopyrimidinedione derivative of formula (I)

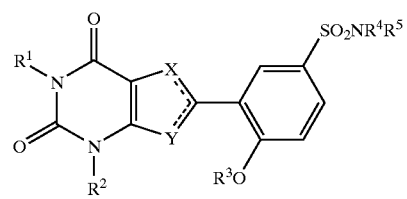

wherein: —X—C—Y— represents

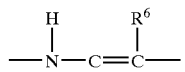

or —X—C—Y— represents

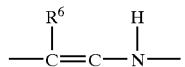

$R^1$, $R^2$ and $R^3$ each independently represent: a hydrogen atom; an alkyl group which is unsubstituted or substituted by one or more hydroxy, alkoxy, alkylthio, amino, mono- or di-alkylamino, hydroxycarbonyl, alkoxycarbonyl, acylamnino, carbamoyl or alkylcarbanioyl groups; or a group of formula

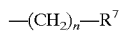

wherein n is an integer from 0 to 4 and $R^7$ represents: a cycloalkyl group; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur. which ring may be unsubstituted or substituted by one or more halogen atoms or hydroxy, phenyl, alkoxycarbonyl, amino, mono-alkylamino, di-alkylarnino or hydroxycarbonyl groups or one or more alkyl groups which may in turn be unsubstituted or substituted by one or more halogen atoms or hydroxy, alkoxy, hydroxyalkoxy, phenyl, alkoxycarbonyl, amino, mono- or di-alkylamino or hydroxycarbonyl groups, either $R^4$ and $R^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or two substituents selected from (a) halogen atoms and hydroxy, oxoalkyl, carbamoyl, hydroxycarbonyl, alkoxycarbonyl, amino, mono- and di-alkylamino groups and (b) alkyl, alkenyl and divalent alkylene groups which may in turn be unsubstituted or substituted by one or more hydroxy, alkoxy, hydroxyalkoxy, amino or mono- or di-alkylamino groups, or $R^4$ and $R^5$ independently represent a hydrogen atom or an alkyl group which may be unsubstituted or substituted by one or more hydroxy, alkoxy, alkylthio, amino, mono- or di-alkylaniino groups, or $R^4$ represents hydrogen or an alkyl group and $R^5$ represents a group of formula —(CH$_2$)$_n$—R$^7$ as defined above, $R^6$ represents a hydrogen or halogen atom, or a nitro or alkoxycarbonyl group, or an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups, or an N-oxide or a pharmaceutically acceptable salt thereof.

2. A 6-phenylpyrrolopyrimidinedione derivative of formula (I), as defined in claim 1, wherein —X—C—Y—, $R_1$, $R_2$, $R_3$ and $R_6$ are as defined in claim 1 and either $R^4$ and $R^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or two halogen atoms or hydroxy, oxoalkyl, carbamoyl, hydroxycarbonyl, alkoxycarbonyl, amino, mono- or di-alkylamino groups or one or two alkyl groups which may in turn be unsubstituted or substituted by one or more hydroxy, alkoxy, hydroxyalkoxy, amino or mono- or di-alkylamino groups, or $R^4$ and $R^5$ independently represent a hydrogen atom or an alkyl group which may be unsubstituted or substituted by one or more hydroxy, alkoxy, alkylthio, amino, mono- or di-alkylamino groups, or $R^4$ represents hydrogen or an alkyl group and $R^5$ represents a group of formula —$(CH_2)_n$—$R^7$ as defined above, or a pharmaceutically acceptable salt thereof.

3. A compound according to claim 1 wherein $R^1$, $R^2$ and $R^3$ independently represent hydrogen or an unsubstituted alkyl group selected from methyl, ethyl, n-propyl, i-propyl, n-butyl, sec-butyl and t-butyl.

4. A compound according to claim 1 wherein $R^6$ represents a hydrogen atom, fluorine atom, chlorine atom, bromine atom, iodine atom, or a methyl group which is unsubstituted or substituted by a dimethylamino or methoxy group.

5. A compound according to claim 1 wherein $R^4$, $R^5$ and the nitrogen atom to which they are attached form a 4, 5, 6 or 7 membered ring comprising a total of from 1 to 3 heteroatoms selected from nitrogen, oxygen or sulphur, which ring may be unsubstituted or substituted by one or more groups selected from hydroxy, carboxy, alkoxy, carbamnoyl, carbaldehyde, alkoxycarbonyl, amino, mono- or di-alkylamino groups and alkyl, alkenyl and divalent alkylene groups which may be unsubstituted or substituted by one or more hydroxy, methoxy, hydroxymethoxy or di-alkylamino groups.

6. A compound according to claim 5 wherein the ring is an unsubstituted or substituted piperidyl, piperazinyl, morpholinyl, diazacycloheptyl, azacyclobutyl, pyrrolidinyl or pyrazolyl group.

7. A compound according to claim 1 wherein $R^4$ represents a hydrogen atom or an alkyl group and $R^5$ is a group of formula —$(CH_2)_n R^7$ wherein n is 0, 1, 2 or 3 and $R^7$ is a group $R^8$ which represents an unsubstituted or substituted morpholinyl, pyridyl, piperidyl, piperazinyl, quinuclidinyl, triazolyl or tetrazolyl group.

8. A compound according to claim 7 wherein $R^8$ is an unsubstituted morpholinyl, pyridyl or piperidyl group, a piperidyl group substituted by 1, 2, 3 or 4 methyl groups or a piperazinyl or quinuclidinyl group substituted at a nitrogen atom by a methyl, ethyl, 2-hydroxyethyl, 2-methoxyethyl, propyl, 3-hydroxypropyl, 3-methoxypropyl, carbaldehyde or ethoxycarbonyl group.

9. A compound according to claim 1 wherein $R^4$ and $R^5$ are independently selected from a hydrogen atom, methyl group, ethyl group or a $C_{1-6}$ alkyl group substituted by one or more halogen atoms or hydroxy, alkoxy, alkylthio, oxo, hydroxycarbonyl, alkoxycarbonyl, carbamoyl, alkylcarbamoyl or mono- or di-alkylamino groups.

10. A compound according to claim 1 wherein $R^4$ is a hydrogen atom or a methyl or 2-hydroxyethyl group.

11. A compound according to claim 1, wherein $R^5$ is a 2-hydroxyethyl, 2-dimethylaminoethyl, 2-pyridylethyl, N-piperidylethyl, 2,2,6,6-tetramethylpiperidin-4-yl, N-morpholinylethyl, N-morpholinylpropyl or N-methyl-N-piperazinyl group.

12. A compound according to claim 1 which is:
3-Methyl-6-[5-(4-methylpiperazine-1-sulphonyl)-2-propoxyphenyl]-1-propyl-1,5-dihydropyrrolo[3,2-d]pyrimidine-2,4-dione,
6-[5-(4-Ethylpiperazine-1-sulphonyl)-2-propoxyphenyl]-3-methyl-1-propyl-1,5-dihydropyrrolo[3,2-d]pyrimidine-2,4-dione,
7-Chloro-6-[2-ethoxy-5-(4-methylpiperazine-1-sulfonyl)phenyl]-3-methyl-1-propyl-1,5-dihydropyrrolo[3,2-d]pyrimidine-2,4-dione,
7-Chloro-3-methyl-6-[5-(4-methylpiperazine-1-sulfonyl)-2-propoxyphenyl]-1-propyl-1,5-dihydropyrrolo[3,2-d]pyrimidine-2,4-dione,
7-Chloro-6-[5-(4-ethylpiperazine-1-sulfonyl)-2-propoxyphenyl]-3-methyl-1-propyl-1,5-dihydropyrrolo[3,2-d]pyrimidine-2,4-dione,
7-Chloro-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione,
7-Bromo-6-{2-ethoxy-5-[4-(3-hydroxypropyl)piperazine-1-sulfonyl]phenyl}-3-methyl-1-propyl-1,5-dihydropyrrolo[3,2-d]pyrimidine-2,4-dione,
7-Bromo-3-methyl-6-[5-(4-methylpiperazine-1-sulfonyl)-2-propoxyphenyl]-1-propyl-1,5-dihydropyrrolo[3,2-d]pyrimidine-2,4-dione,
7-Bromo-6-{5-[4-(2-hydroxyethyl)piperazine-1-sulfonyl]-2-propoxyphenyl}-3-methyl-1-propyl-1,5-dihydropyrrolo[3,2-d]pyrimidine-2,4-dione, or
7-Bromo-6-{5-[4-(3-hydroxypropyl)piperazine-1-sulfonyl]-2-propoxyphenyl}-3-methyl-1-propyl-1,5-dihydropyrrolo[3,2-d]pyrimidine-2,4-dione,
or a pharmaceutically acceptable salt thereof.

13. A compound of formula (IV)

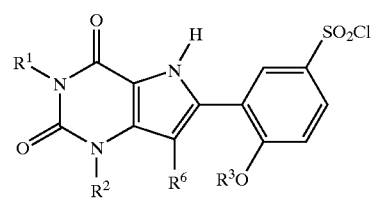

(IV)

wherein $R^1$, $R^2$ and $R^3$ each independently represent: a hydrogen atom; an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups; or a group of formula —(CH$_2$)$_n$—R$^7$ wherein n is an integer from 0 to 4 and R$^7$ represents: a cycloalkyl group; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, phenyl, alkoxycarbonyl, amino, mono-alkylamino, di-alkylamino or hydroxycarbonyl groups or one or more alkyl groups which may in turn be unsubstituted or substituted by one or more halogen atoms or hydroxy, alkoxy, hydroxyalkoxy, phenyl, alkoxycarbonyl, amino, mono- or di-alkylamino or hydroxycarbonyl groups, and R$^6$ represents a hydrogen or halogen atom, or a nitro or alkoxycarbonyl group, or an alkyl group which is unsubstituted or substituted by one or more hydroxy, alkoxy, alkylthio, amino, mono- or di-alkyamino, hydroxycarbonyl, alkoxycarbonyl, acylamino, carbamoyl or akylcarbamoyl groups.

14. A composition comprising a compound according to claim 1 in admixture with a pharmaceutically acceptable carrier or diluent.

15. A process for the preparation of a compound of formula (I)

(I)

wherein: —X—C—Y— represents and R$^1$, R$^2$, R$^3$, R$^4$, R$^5$, R$^6$ and R$^7$ are as defined in claim 1, which process comprises reacting a sulphonyl chloride of formula (IV):

(IV)

wherein R$^1$, R$^2$, R$^3$ and R$^6$ are as defined in claim 1, with an amine of formula (V):

(V)

wherein R$^4$ and R$^5$ as defined in claim 1.

16. A process for the preparation of a compound of formula (I)

(I)

wherein: —X—C—Y— represents and R$^1$, R$^2$, R$^3$, R$^4$, R$^5$, R$^6$ and R$^7$ are as defined in claim 1, which process comprises condensing a 6-aminouracil of formula (IX):

(IX)

wherein R$^1$ and R$^2$ are as defined in claim 1, with a bromoacetophenone of formula (X):

(X)

wherein R$^3$, R$^4$ and R$^5$ are as defined in claim 1.

* * * * *